US012318503B2

(12) United States Patent
Maji et al.

(10) Patent No.: US 12,318,503 B2
(45) Date of Patent: Jun. 3, 2025

(54) FUNCTIONAL AMYLOID HYDROGELS AND APPLICATIONS THEREOF

(71) Applicant: Indian Institute of Technology Bombay, Mumbai (IN)

(72) Inventors: Samir K. Maji, Mumbai (IN); Namrata Singh, Mumbai (IN); Komal Patel, Mumbai (IN); Reeba Susan Jacob, Mumbai (IN)

(73) Assignee: INDIAN INSTITUTE OF TECHNOLOGY BOMBAY, Mumbai (IN)

( * ) Notice: Subject to any disclaimer, the term of this patent is extended or adjusted under 35 U.S.C. 154(b) by 727 days.

(21) Appl. No.: 17/263,278

(22) PCT Filed: Jan. 3, 2020

(86) PCT No.: PCT/IB2020/050026
§ 371 (c)(1),
(2) Date: Jan. 26, 2021

(87) PCT Pub. No.: WO2020/141480
PCT Pub. Date: Jul. 9, 2020

(65) Prior Publication Data
US 2021/0322628 A1    Oct. 21, 2021

(30) Foreign Application Priority Data

Jan. 4, 2019 (IN) .............................. 201921000523

(51) Int. Cl.
*A61L 26/00* (2006.01)
(52) U.S. Cl.
CPC ......... *A61L 26/008* (2013.01); *A61L 26/0028* (2013.01); *A61L 26/0066* (2013.01);
(Continued)

(58) Field of Classification Search
None
See application file for complete search history.

(56) References Cited

U.S. PATENT DOCUMENTS

| 7,851,434 B2 | 12/2010 | Jarvis et al. |
| 10,004,828 B2 | 6/2018 | Gazit et al. |

(Continued)

FOREIGN PATENT DOCUMENTS

| CN | 102558304 A | 7/2012 |
| WO | 2011112856 A2 | 9/2011 |
| WO | 2014116187 A1 | 7/2014 |

OTHER PUBLICATIONS

Das et al., Biomacromolecules 19(6): 1826-1839 (2018).*
(Continued)

*Primary Examiner* — Erin M. Bowers
(74) *Attorney, Agent, or Firm* — CANTOR COLBURN LLP

(57) ABSTRACT

The present invention relates to the formation of hydrogels from poly-amino acids designed from the β-aggregation-prone region of functional amyloidogenic proteins that self-assemble to form a three-dimensional nanofibril matrix. Further, these water entrapped meshwork can be modulated by various physico-chemical cues. The present invention also explores the use of the designed hydrogels as cell and tissue adhesive biomaterial for tissue engineering applications. The present invention also relates to the application of functional amyloid hydrogel including but not limited to 3D tumoroid model for anticancer drug testing, optimization of drug dosage including drug-resistant tumors, repurposing of existing drugs, and patient-derived organoid. The present invention also describes the use of functional amyloid hydrogel as a depot for controlled and sustained release of therapeutics and biologic agents encapsulated within the (Continued)

same. The present invention also provides a moist highly water retentive material as reservoir of wound exudates thereby promotes healing.

19 Claims, 28 Drawing Sheets

Specification includes a Sequence Listing.

(52) U.S. Cl.
CPC ............... *A61L 2300/252* (2013.01); *A61L 2300/414* (2013.01); *A61L 2400/12* (2013.01)

(56) References Cited

U.S. PATENT DOCUMENTS

2015/0320865 A1  11/2015  Hantash et al.
2016/0115196 A1  4/2016  Fichman et al.

OTHER PUBLICATIONS

Jacob et al., Biomaterials 54: 97-105 (2015).*
Jacob et al., J. Biol. Chem. 291(10): 5278-5298 (2016).*
International Search Report and Written Opinion for International Application PCT/IB2020/050026; International Filing Date: Jan. 3, 2020; Date of Mailing: Mar. 31, 2020; 10 pages.

* cited by examiner

FA1

SEQUENCE LISTING

```
<160> NUMBER OF SEQ ID NOS: 6

<210> SEQ ID NO 1
<211> LENGTH: 5
<212> TYPE: PRT
<213> ORGANISM: artificial
<220> FEATURE:
<223> OTHER INFORMATION: functional amyloid nano-fibril peptide-FA1

<400> SEQUENCE: 1

Lys Leu Met Glu Ile
1               5

<210> SEQ ID NO 2
<211> LENGTH: 5
<212> TYPE: PRT
<213> ORGANISM: artificial
<220> FEATURE:
<223> OTHER INFORMATION: functional amyloid nano-fibril peptide-FA2

<400> SEQUENCE: 2

Lys Leu Leu Asp Ile
1               5

<210> SEQ ID NO 3
<211> LENGTH: 5
<212> TYPE: PRT
<213> ORGANISM: artificial
<220> FEATURE:
<223> OTHER INFORMATION: functional amyloid nano-fibril peptide-FA3

<400> SEQUENCE: 3

Ala Val Val Leu Ser
1               5

<210> SEQ ID NO 4
<211> LENGTH: 5
<212> TYPE: PRT
<213> ORGANISM: artificial
<220> FEATURE:
<223> OTHER INFORMATION: functional amyloid nano-fibril peptide-FA4
```

-continued

```
<400> SEQUENCE: 4

Phe Val Gln Trp Leu
1               5

<210> SEQ ID NO 5
<211> LENGTH: 5
<212> TYPE: PRT
<213> ORGANISM: artificial
<220> FEATURE:
<223> OTHER INFORMATION: functional amyloid nano-fibril peptide-FA5

<400> SEQUENCE: 5

Asn Leu Leu Phe Asn
1               5

<210> SEQ ID NO 6
<211> LENGTH: 5
<212> TYPE: PRT
<213> ORGANISM: artificial
<220> FEATURE:
<223> OTHER INFORMATION: functional amyloid nano-fibril peptide-FA6

<400> SEQUENCE: 6

Leu Val Thr Leu Phe
1               5
```

FUNCTIONAL AMYLOID HYDROGELS AND APPLICATIONS THEREOF

CROSS REFERENCE TO RELATED APPLICATIONS

This application is a National Stage application of PCT/IB2020/050026, filed Jan. 3, 2020, which claims the benefit of priority to Indian Patent Application No. 201921000523, filed Jan. 4, 2019, both of which are incorporated by reference in their entirety herein.

FIELD OF INVENTION

The present invention relates to functional amyloid hydrogels, which are peptide-based gels, where the component peptides can self-assemble into cross-β sheet rich amyloid, non-toxic nanofibrils and to the methods of generating the same. These functional amyloid nanofibrils can assemble into a three-dimensional nanofibrous meshwork, which adopts the shape of the vessel that it holds and can mimic features of the natural extracellular matrix. Moreover, these peptides can self-assemble into hydrogels by adjusting the pH, temperature and salt and/or ion composition of the peptide solution. The present invention also relates to uses thereof in applications such as three-dimensional tumoroid model, drug delivery, cell adhesion, tissue engineering, wound healing and more.

BACKGROUND AND PRIOR ART

A hydrogel is a macromolecular gel comprising a network of cross-linked polymer chains with encapsulated water molecules. They are mainly synthesized from hydrophilic monomers either by a chain or a stepwise reaction, in presence of a functional cross-linker to facilitate the network formation (Ahmed et al 2015, Hydrogel: Preparation, characterization, and applications: A review. Journal of advanced research, 6(2), 105-121). A meshwork-like structure enhances the hydrogels ability to absorb large amounts of water molecules via hydrogen bonding. This subsequently results in the development of a hydrogel with characteristic visco-elastic mechanical properties resembling the living tissues to a great extent (Kohane et al 2008, Hydrogels in drug delivery: Progress and challenges. Polymer, 49(8), 1993-2007).

Hydrogels can be categorized as chemical or physical gels, based on the nature of the cross-linking process. In chemical hydrogels, the overall facets are contributed by the structure and properties of the primary chains, as well as by the cross-linking density. Physical gels form a network by molecular interactions and can be modulated by factors such as temperature, pH, ionic strength and mechanical stress. This class of hydrogels can be reversible in nature. They could be developed from polysaccharide, synthetic polymers, proteins and other poly-amino acids through the process of molecular self-assembly. Peptide hydrogels are a class of physical hydrogel, where the monomeric components self-assemble to form a supramolecular structure or a defined 3D structure. The water retention ability of the hydrogel enables it to mimic the living body tissues better than any other material used for tissue regeneration applications. Additionally, protein/peptide scaffolds are structurally very similar to the extracellular matrices of many of the tissues. They exhibit simple and distinct structural elements, adjustable mechanical properties, as well as high biocompatibility and biodegradability. The self-assembling peptide hydrogel is one of the most established hydrogels with significant advantages over a wide range of applications such as three-dimensional (3D) cell culture, tissue engineering, anti-tumor therapy, drug delivery and controlled release (Caliari et al 2016, A practical guide to hydrogels for cell culture. Nature methods, 13(5), 405; Thiele et al 2014, 25th anniversary article: designer hydrogels for cell cultures: a materials selection guide. Advanced materials, 26(1), 125-148; and Yunfeng et al 2018 Hydrogel microenvironments for cancer spheroid growth and drug screening. Science Advances Vol. 4, no. 4, eaas8998). The high biocompatibility and low immunogenic property enable the use of these hydrogels for various medical applications (Jacob et. al 2016, Cell Adhesion on Amyloid Fibrils Lacking Integrin Recognition Motif. J Biol Chem. 2016; 291(10):5278-5298. doi:10.1074/jbc.M115.678177; Das et. al 2016, Implantable amyloid hydrogels for promoting stem cell differentiation to neurons. NPG Asia Materials 8, no. 9 (2016): e304; and Das et. al 2018, Amyloid fibrils: Versatile biomaterials for cell adhesion and tissue engineering applications. Biomacromolecules, 19(6), 1826-1839). The areas where active research is currently being conducted include:
- Absorbable Sutures
- Cell adhesion, tissue engineering and regeneration purposes
- Three-dimensional in vitro tumor model
- Drug delivery
- Wound healing Amyloids (Diseased and Functional)

Amyloids are highly ordered protein/peptide aggregates with cross-β-sheet structure. Generally, amyloids have been associated with various disease conditions such as Alzheimer's disease (AD), Type II diabetes, prion diseases, and Parkinson's disease (PD) (Chiti et al 2006, Protein misfolding, functional amyloid, and human disease. Annu. Rev. Biochem., 75, 333-366; and Chiti et al 2017, Protein misfolding, amyloid formation, and human disease: a summary of progress over the last decade. Annual review of biochemistry, 86, 27-68). Recent studies suggest that during protein aggregation, mature fibrils are less toxic as compared to intermediate oligomeric protein assemblies. In disease-associated amyloids, aberrant protein misfolding leads to protein aggregation (Uversky et al 2004, Conformational constraints for amyloid fibrillation: the importance of being unfolded. Biochimica et Biophysica Acta (BBA)-Proteins and Proteomics, 1698(2), 131-153; and Knowles et al 2007, Role of intermolecular forces in defining material properties of protein nanofibrils. Science, 318(5858), 1900-1903). However, amyloid state of certain proteins in the host organism performs native biological functions and is termed as functional amyloids (Fowler et al 2007, Functional amyloid—from bacteria to humans. Trends in biochemical sciences, 32(5), 217-224; Barnhart et al 2006, Curli biogenesis and function. Annu. Rev. Microbiol., 60, 131-147; True et al 2000, A yeast prion provides a mechanism for genetic variation and phenotypic diversity. Nature, 407(6803), 477; and Maji et al 2009, Functional amyloids as natural storage of peptide hormones in pituitary secretory granules. Science, 325(5938), 328-332). The formation of such functional amyloid assemblies is highly dynamic and specifically regulated to avoid the accumulation of toxic oligomers. Structurally, amyloids are highly ordered and stable structures that are resistant to proteases and adverse environmental conditions (Fowler et al 2007 and Smith et al 2006, Characterization of the nanoscale properties of individual amyloid fibrils. Proceedings of the National Academy of Sciences, 103(43), 15806-15811). The high tensile strength, mechanical stiffness and suitability to tune the physicochemical properties of amyloid by modulating amino acid sequences make amyloid a potential candidate for numerous biotechnological applications (Cherny et al 2008, Amyloids: not only pathological agents but also ordered nanomaterials. Angewandte Chemie International Edition, 47(22), 4062-4069; Gras et al 2008, Functionalised amyloid fibrils for roles in cell adhesion. Biomaterials 29, 1553-1562; and Wei et al 2017, Self-assembling peptide and protein amyloids: from structure to tailored function in nanotechnology. Chemical Society Reviews, 46(15), 4661-4708). Moreover, easy functionalization of fibrils for specific applications and the ability to form higher order complexes such as filaments, gels and films makes it suitable for immobilizing enzymes, small molecules and drugs.

Amyloids for Cell Adhesion and Tissue Engineering

Amyloids exhibit unique surface topography due to its repetitive arrangement of uncharged and charged residues (Nilsson et al 2009, Small organic probes as amyloid specific ligands—past and recent molecular scaffolds. FEBS Lett. 583 (16), 2593-9; Calamai el al 2006, Nature and significance of the interactions between amyloid fibrils and biological polyelectrolytes. Biochemistry 45 (42), 12806-15; Ghosh el al 2014, Complexation of amyloid fibrils with charged conjugated polymers. Langmuir 30 (13), 3775-86; and Solomon el al 2011, Heparin binds 8 kDa gelsolin cross-beta-sheet oligomers and accelerates amyloidogenesis by hastening fibril extension. Biochemistry 50(13), 2486-98). Many lower organisms make use of this adhesive property for host surface adhesion and colonization (Chapman el al 2002, Role of *Escherichia coli* curli operons in directing amyloid fiber formation. Science 295 (5556), 851-5; Sullan et al 2009 Nanoscale structures and mechanics of barnacle cement. Biofouling 25 (3), 263-75 and Barlow et al (2010), Characterization of the Adhesive Plaque of the Barnacle Balanusamphitrite: Amyloid-Like Nanofibrils Are a Major Component. Langmuir 26 (9), 6549-6556. In higher organisms, extracellular matrix is a fundamental part of a tissue system in vivo and it provides support to the cells and functions as a local depot for growth factors and hence, regulates cellular dynamics (Langer, 2000, Biomaterials in drug delivery and tissue engineering: one laboratory's experience. AccChem Res 33, 94-101; Langer and Tirrell, 2004, Designing materials for biology and medicine. Nature 428, 487-492; Lutolf and Hubbell, 2005, Synthetic biomaterials as instructive extracellular microenvironments for morphogenesis in tissue engineering. Nat Biotechnol 23, 47-55). A major obstacle in the tissue engineering field is the need for an optimal biomaterial whose properties will closely mimic the microenvironment of a particular cell type. Amyloid fibrils made from peptide/proteins with or without tagged functional moieties and/or fibrils immobilized with functional protein/peptides can be used as scaffolds for promoting cell attachment and growth (Jacob et al 2016 and Reynolds et al 2014, Engineered lysozyme amyloid fibril networks support cellular growth and spreading. Biomacromolecules, 15(2), 599-608). Recently, Gras and co-workers (2008) reported that amyloid fibrils made from the partial amino acid sequence of the transthyretin containing the RGD ligands on the fibril surface provide accessibility for cell adhesion. The design of such functionalized fibrils can be exploited to promote interactions with a wide variety of cell types. Also, understanding the amyloid structure at atomic resolution made it possible to design amyloid fibrils with minimal protein/peptide sequence, which could be harnessed for fabricating scaffolds suitable for both soft as well as hard tissue engineering. Maji and co-workers had recently reported amyloid hydrogels designed from the C-terminus of amyloid-β (Aβ) protein and alpha-synuclein associated with AD and PD, respectively. In these studies, the designed short di-, tri- and penta peptides were capped with an Fmoc group at the N-terminus. It was proposed that rapid intermolecular association of these peptide monomers leads to the formation of amyloid fibrils that eventually entrap the solvent resulting into a hydrogel (Jacob et. al 2016 and Das et. al 2016). In an earlier study, Bolisetty et al (2012), Gelation, phase behavior, and dynamics of β-lactoglobulin amyloid fibrils at varying concentrations and ionic strengths. Biomacromolecules 13.10: 3241-3252 also reported the thixotropicity or self-healing nature of amyloid hydrogels derived from β-lactoglobulin fibrils.

Scaffolds for Organoids, Spheroids and 3D Cell Culture

Scaffolds act as three-dimensional artificial templates in which the tissue targeted for reconstruction is cultured in vitro. The high porosity of the hydrogels allows diffusion of cells during migration, as well as the transfer of nutrients and waste products away from cellular membranes. Conventionally, two-dimensional cell cultures used for testing the effects of anti-cancer agents are simple and convenient, but they present significant limitations in reproducing the complexity and pathophysiology of the in vivo tumor tissue thus posing a major concern. In general, the preclinical validation process in cancer drug discovery comprises a series of primary biochemical and cell-based assays, followed by evaluation in animal tumor models. However, there is a higher rate of attrition and less than 10% of identified potential drug become licensed owing to wrong/less reliable testing platforms. In 2D culture system, the drug formulations provided in the media are accessible to the cells directly and hence it does not account for the diffusion rate and relative drug concentration encountered by the tumor tissue in vivo. In this context, the 3D culture of cells is more reliable and essential for testing cancer therapeutics.

An example for such a 3D cell culture system is spheroids, which are aggregates of cells assuming a spherical shape. Cancer cells are closely packed in spheroids with minute space in between and hence mimic the architecture and the complex intercellular network of solid tumors. There are several 3D in vitro tumor models available, however, a major lacuna in cancer therapeutics is lack of a robust and reliable model, which mimics the native tumor architecture and microenvironment (Rodenhizer 2018, The current landscape of 3D in vitro tumor models: What cancer hallmarks are accessible for drug discovery. Advanced healthcare materials, 7(8), 1701174). The thixotropic nature and the gel-sol interconversion of the functional amyloid hydrogel by vortexing method makes it a distinguishable class of biomaterial to serve as a scaffold for generating three-dimensional cell culture systems including spheroids. Moreover, functional amyloid hydrogel as 3D culture systems provides a robust but controllable environment to study the growth and response of cells to intrinsic (cell signaling, gene expression) and extrinsic (anti-cancer drugs, differentiation factors) biochemical cues. These models will serve as more reliable platforms for evaluating the effects of chemotherapeutic agents and their pharmacokinetic properties in a cancer-like milieu. The recent developments clearly indicate that the shift from 2D to 3D cell cultures for industrial applications is encouraging, but the development of a successful technology, which is also cost-effective, still impose a hurdle, which needs to be resolved before adopting this technology.

Scaffolds for Drug Delivery

Therapeutics of peptide/protein or small molecule origin exhibit short half-life and low bioavailability. Therefore, there is a need for diffusion pumps, chips, subcutaneous administration, infusion pumps or frequent injections for their delivery (Langer 1998, Drug delivery and targeting. Nature 392, 5-10; Langer 2001, Drug delivery. Drugs on target. Science 293, 58-59). As an alternate strategy, biodegradable hydrogels, microspheres, liposomes and polymeric depots may serve as delivering agents (Langer 1998, Langer 2001, Langer 1990, New methods of drug delivery. Science 249, 1527-1533). However, the starting material used for its nanofabrication is derived from both chemical and natural sources. The delivery systems designed from chemical origin are non-biodegradable and exhibit immunogenicity (Langer 2000, Biomaterials in drug delivery and tissue engineering: one laboratory's experience. AccChem Res 33, 94-101; Hubbell 1995, Biomaterials in tissue engineering. Biotechnology (N Y) 13, 565-576). Moreover, the physical, chemical and mechanical properties of self-assembled peptide/protein can be tailored by altering the amino acid residues and/or by varying parameters such as temperature, pH and pressure. RADA16 self-assembled peptide may serve as slow delivery agent for a number of proteins such as trypsin inhibitor, BSA, IgG. Similarly, β2-microglobulin amyloid fibrils were used to design high tensile nanoporous matrix for tissue engineering and drug delivery applications (Nagai et al 2006, Slow release of molecules in self assembling peptide nanofiber scaffold. J Control Release 115, 18-25; Koutsopoulos et al 2009, Controlled release of functional proteins through designer self-assembling peptide nanofiber hydrogel scaffold. Proc Natl Acad Sci USA 106, 4623-4628; Ahn et al 2010, Nanoporous protein matrix made of amyloid fibrils of β2-microglobulin. Biotechnol Prog 26, 1759-1764). Yet in another example where hydrogel was developed from alpha-synuclein fibrils it was used for enzyme encapsulation. The supramolecular assembly of amyloid hydrogel may entrap and encapsulate small molecules, peptides, proteins therapeutic agents and other biological molecules (Bhak et al 2010, Amyloid hydrogel derived from curly protein fibrils of alpha-synuclein. Biomaterials 31, 5986-5995). The encapsulated payload will be protected from various physical and chemical factors in the stable core of the amyloid hydrogel and may aid in controlled and sustained release for an extended time period. Protein/peptides are in general administered by the subcutaneous route, as they are susceptible to gastric enzymes. Many peptide treatments such as somatostatin, insulin, LHRH, need continuous or repeated injections. However, this strategy is both inconvenient and is not patient compliant. Alternatively, solid polymeric matrix and microcapsules have been developed to ensure prolonged release. Some polymeric hydrogels made up of NIPA, cellulose ether, agarose, lecithin and hyaluronate have been developed to control the delivery of the payload.

Scaffolds for Wound Healing:

Chronic wound care has been gaining momentum due to drug delivery with the use of growth factors or antibacterial compounds encapsulated in scaffolds. This approach leads to wound healing in the epithelial cells, and has also proven to promote wound closure. Hydrogels can serve as a vehicle that delivers the desired substance into the exact location needed for wound healing. In situ forming hydrogels that rapidly cross-link with tissues have drawn significant attention as potent bioadhesive materials (Blacklow et al 2019, Bioinspired mechanically active adhesive dressings to accelerate wound closure. Science advances, 5(7), eaaw3963). These materials are required to carry out a variety of functions, such as stopping unwanted bleeding, i.e., as hemostatic agents; binding tissues together, i.e., as bioadhesives; and if possible, facilitating a rapid healing process. Considerable efforts have been given to develop naturally derived tissue adhesives, e.g., directly extracted from biological sources (fibrin glues), proteins (gelatin based glues), carbohydrates (alginate), or synthetic material-based adhesives (cyanoacrylates), poly(ethylene glycol)-based bioadhesives, etc. However, traditional bioadhesives normally suffer from either relatively poor adhesive strength or higher toxicity. The value of hydrogels as biomaterials lies in the similarity of their physical properties to those of living tissues. But the currently available hydrogel systems of both chemical and biological origin have many of the following limitations such as they cannot limit bacterial infection, proper gaseous exchange and most importantly exhibit mechanical instability. The presently available hydrogel systems exhibit disadvantages such as poor mechanical stability at swollen state, semi-transparent nature, semi-permeability to gases and water vapor and poor bacterial barrier. Amyloid hydrogel being robust with high tensile strength and mechanical stability would result in controlled drug release for preventing bacterial contamination and rapid wound healing.

WO2014/116187 relates to hydrogels comprising a plurality of amphiphilic peptides and/or peptides capable of self-assembling into three-dimensional macromolecular nano-fibrous networks, which entrap water and form said hydrogels, wherein at least a portion of said plurality of amphiphilic peptides and/or peptides is chemically cross-linked. The invention further relates to methods for preparing such hydrogels and to various uses of such hydrogels, e.g. as cell culture substrates, for drug and gene delivery, as wound dressing, as an implant, as an injectable agent that gels in situ, in pharmaceutical or cosmetic compositions, in regenerative medicine, in tissue engineering and tissue regeneration, or in electronic devices. It also relates to a method of tissue regeneration or tissue replacement using a hydrogel in accordance with the present invention.

US20160115196 relates to self-assembled bioadhesive, anti-microbial, anti-fouling and/or anti-oxidant micro- and nanostructures comprising a plurality of amino acids or peptides, the micro- or nano-structures comprising at least one aromatic amino acid comprising a catecholic moiety. The invention further relates to methods of preparing the self-assembled micro- and nano-structures and to their use in a variety of biomedical and industrial applications, for example in pharmaceutical and cosmetic compositions and in medical devices. According to some embodiments, the micro- or nano-structure of the present invention may be used in the preparation of a pharmaceutical composition, a cosmetic composition, or a medical device (e.g., a medical sealant or adhesive such as an adhesive patch or band-aid). In other embodiments, the micro- and nano-structures of the invention are applied as a coating (e.g., an adhesive coating) to an existing medical device. Other utilities include but are not limited to a drug delivery vehicle, a 3D scaffold for cell growth, tissue adhesive for regenerative medicine, biological glue that is resilient to the shear forces of blood flow, antibacterial and antioxidant uses, or any combination of the foregoing.

WO2011112856 showcases novel peptides that can form hydrogels and methods of making such hydrogels. The invention includes the design of a peptide comprising of a hydrophobic region joined to a hydrophilic region by turning region, which can be triggered to form hydrogel. The patent also includes methods of gel synthesis from peptide solutions with varying percentages of the peptide component and triggering gel formation either by adjusting pH or addition of cations.

US20150320865 teaches new hybrid hydrogel scaffolds comprised of a polyoxyethylene-polyoxypropylene (block) copolymer (a "poloxamer") and a self-assembling peptide, which maintain the mechanical and bioactive properties of its individual constituents (as compared to when the individual constituents are scaffolds or hydrogels by themselves). The hydrogels of the invention can include a combination of materials from different origins or with different properties that provide a hybrid material that meets the multiple needs of a scaffold for tissue engineering. The invention thus provides new hybrid hydrogel scaffolds comprised of a polyoxyethylene-polyoxypropylene (block) copolymer (referred to herein as a "poloxamer") and a self-assembling peptide, which maintain the mechanical and bioactive properties of its individual constituents (as compared to when the individual constituents are scaffolds or hydrogels by themselves). As used herein, a "hybrid hydrogel" includes at least one poloxamer and at least one self-assembling peptide.

CN102558304 discloses self-assembling peptide and application of the self-assembling peptide for promoting a tumor cell to form a multicellular spheroid. The self-assembling peptide comprises an amino acid segment consisting of 3 to 20 continuous hydrophobic amino acids; specific peptides are connected to an N tail end or a C tail end of the amino acid segment or both the N tail end and the C tail end of the amino acid segment; and the sequence of the specific peptide is GYRGDS, GYRGDSPRGDS, YRGDS, PFSSTKT, SKPPGTSS, YRGDSPRGDS OR PRGDS.

U.S. Ser. No. 10/004,828 discloses a hydrogel comprising a fibrous network of a plurality of peptides, wherein each peptide in the plurality of peptides has an amino acid sequence not exceeding 6 amino acids in length, whereas the amino acid sequence comprises at least one aromatic amino acid residue. Each of the peptides in the plurality of peptides can, therefore, have two, three, four, five or six amino acid residues. According to further features in preferred embodiments of the invention, at least one peptide in the plurality of peptides is an end-capping modified peptide. According to still further features in the described preferred embodiments the aromatic end-capping moiety is selected from the group consisting of 9-fluorenylmethyloxycarbonyl (Fmoc) and benzyloxycarbonyl (Cbz). The inventors have previously uncovered that a remarkably short peptide, the diphenylalanine aromatic core of the β-amyloid polypeptide, efficiently self-assembles into a novel class of peptide nanotubes.

U.S. Pat. No. 7,851,434B2 relates to describing methods, applications, compositions consisting of amyloid-like materials made from fruit or vegetable proteins, which impart higher mechanical strength to the employed material. It also discloses the formation of synthetic amyloid-like proteins or fibrils in vitro and in vivo. It describes compositions such as scaffolds, coating material, adhesive sealants and composite material. Another aspect of the invention relates to the role of amyloid in inhibition of bonding.

Self-Assembling Peptide and Protein Amyloids: From Structure to Tailored Function in Nanotechnology; Gang Wei, Zhigiang Su, Nicholas P. Reynolds, Paolo Arosio, Ian W. Hamley, Ehud Gazit and Raffaele Mezzenga; Chem. Soc. Rev., Issue 15(46), 2017, 4661-4708

In this review, the recent progress made in the field of functional and artificial amyloids have been highlighted. The connections between protein/peptide folding, unfolding and aggregation mechanisms, which finally results into the amyloid structure and contribute to its functionality has been discussed. They also highlight the current advancement in the design and synthesis of amyloid biological and functional materials and identify new potential fields in which amyloid structures exhibit potential breakthroughs.

Self-Assembled Fmoc-Peptides as a Platform for the Formation of Nanostructures and Hydrogels, R Orbach et al., Biomacromolecules, Vol. 10 (9), 2646-2641; 2009

In this study a library of natural and synthetic aromatic Fmoc-dipeptides was screened. The distinctive molecular and physical properties of the designed peptides were characterized. Moreover, the fabrication of the bioactive RGD sequence into a hydrogel is also included. This study offers new opportunities for developing cell-adhesive hydrogel scaffolds for biomedical applications, as well as for establishing strategies to modify surfaces with bioactive materials.

Short-Peptide Based Self-Assembled Nanostructures: Implications in Drug Delivery and Tissue Engineering; JibanJyoti Panda, Virander Singh Chouhan; Polymer Chemistry; Issue 15(5), 2014, 4418-4436

The review explains how self-assembly of biomolecules facilitates the creation of a diverse range of hierarchical nanostructures from a wide range of polymeric and non-polymeric materials. Peptides and specifically short peptides are very attractive in this respect due to their unmatched biocompatibility, ease of synthesis, functionality as well as tunable bioactivity along with the availability of rich chemistry for fine-tuning the structure and function of peptides according to environmental conditions. Self-assembled peptide-based nanostructures such as tubes, filaments, fibrils, hydrogels, vesicles, and monolayers have been studied by many research groups and found application as three-dimensional cell growing scaffolds, dental implants, neural tissue engineering scaffolds and as carriers for drugs, proteins and genes, and nucleotides. Nanostructures are also being developed from designed or modified amino acids to have enhanced cellular as well as in vivo stability. These modified nanostructures showed enhanced drug delivery properties both under in vivo and in vitro conditions.

An opportunity and need exists for the designing and development of novel hydrogel scaffold strategies, as there still remains a need for rigid, tunable, porous, thixotropic, cytocompatible, simple and inexpensive hydrogel that is formed instantaneously both in vitro and in vivo. Also, there is a need for a hydrogel, which will provide a multi-purpose platform for various applications such as cell adhesion, tissue engineering, tumoroid/organoid model, drug delivery, wound healing and more.

OBJECT OF THE PRESENT INVENTION

It is an object of the present invention to overcome the drawbacks of the prior art.

It is another object of the present invention to provide a small peptide hydrogel designed from functional amyloids, which can self-assemble to form a nanofiber matrix.

It is another object of the present invention to provide a method for developing a scaffold from functional amyloids for cell adhesion and tissue engineering applications.

It is another object of the present invention to provide an easy-to-use, inexpensive, and scalable technology for production of complex-shaped, spheroid and/or tumoroid model capable of mimicking in vivo milieu.

It is yet another object of the present invention to provide a method of using the functional amyloid hydrogel for delivering active biological agents by encapsulating the same in it and exhibiting controlled and sustained release of the biologic agent.

It is a further object of the present invention to provide a method of developing the functional amyloid hydrogel as a wound healer.

SUMMARY OF THE PRESENT INVENTION

The following presents a simplified summary of the invention in order to provide a basic understanding of some aspects of the invention. This summary is not an extensive overview of the present invention. It is not intended to identify the key/critical elements of the invention or to delineate the scope of the invention.

In an aspect of the present invention, there is provided functional amyloid hydrogels comprising of functional amyloid nano-fibril peptides having sequences selected from the group consisting of KLMEI, KLLDI, AVVLS, FVQWL, NLLFN and LVTLF.

In an aspect of the present invention, there is provided a method of preparing the hydrogels, the method comprising the steps of
a. preparing a solution comprising peptide having sequences selected from the group consisting of KLMEI, KLLDI, AVVLS, FVQWL, and NLLFN and LVTLF;
b. altering one or more chemical or physical characteristic of the solution, to obtain a hydrogel, wherein the characteristic is selected from a group comprising temperature, pH and ionic strength.

In yet another aspect of the invention, there is provided a method for developing a scaffold for cell adhesion, the method comprising growing of cells on the functional amyloid hydrogels as described herein.

In another aspect of the invention, there is provided a method for developing spheroids and/or tumoroid for use as 3-dimensional tumor models, the method comprising:
a. dissolving the functional amyloid hydrogels as described herein to obtain a solution of the hydrogel;
b. mixing the solution of the hydrogel with cells and incubating the cell-hydrogel mixture; and
c. culturing the mixture containing solidified hydrogel in a suitable medium to obtain the spheroids and/or tumoroid.

In yet another aspect of the present invention, there is provided a method for developing a delivery agent for a biologic, the method comprising of:
a. dissolving the functional amyloid hydrogels as described herein to obtain a solution of the hydrogel;
b. mixing a biologic with the solution of the hydrogel to obtain a mixture solution; and
c. maintaining the mixture solution at room temperature for 10-30 mins to obtain the delivery agent for a biologic.

In a further aspect of the present invention, there is provided a method for developing a wound healer comprising functional amyloid hydrogel as described herein, wherein the functional amyloid hydrogel comprises biological agents.

BRIEF DESCRIPTION OF THE ACCOMPANYING FIGURES

The above and other aspects, features and advantages of the embodiments of the present disclosure will be more apparent in the following description taken in conjunction with the accompanying drawings, in which:

FIG. 1 depicts the general design scheme of the functional amyloid hydrogel and its applications.

FIGS. 2A, B and C show the biophysical characterization of the hydrogel. FIG. 2A depicts the Congo red binding ability of the designed hydrogel. FIG. 2B shows the Thioflavin T (ThT) binding assay revealing high binding of ThT to amyloid fibrils of the hydrogels. FIG. 2C depicts the FTIR spectra of the peptide components of the hydrogels.

Figure 8A:
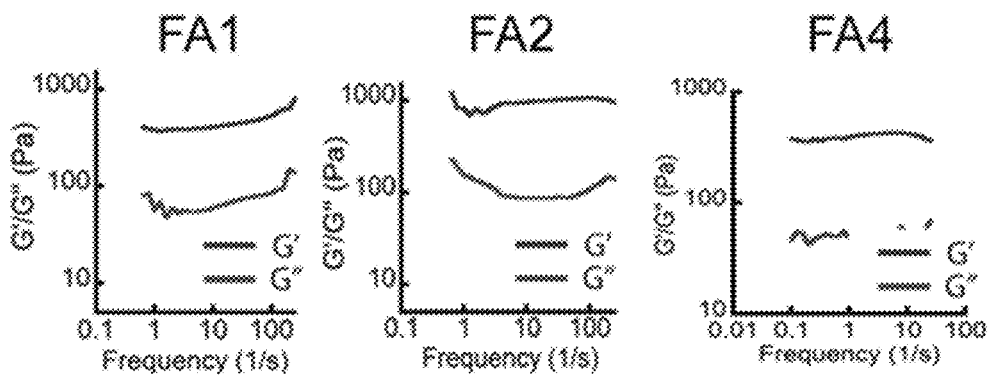
Figure 8B:
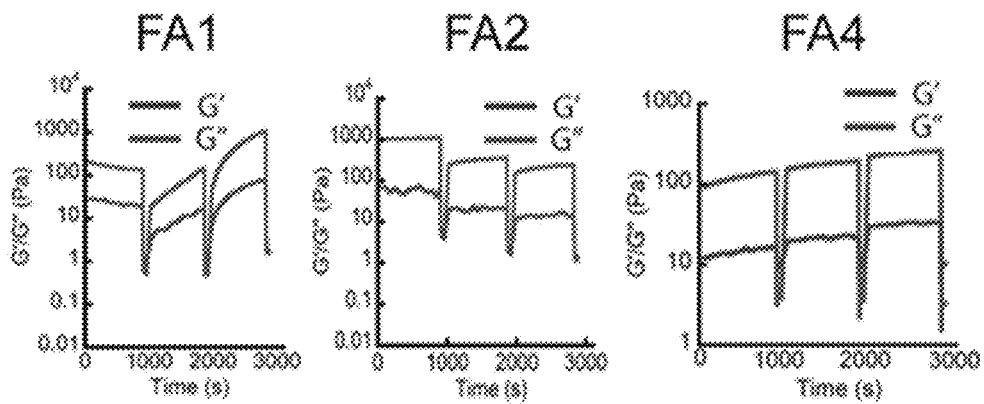

FIGS. 8A and B show the rheological properties of the functional amyloid hydrogels. FIG. 8A shows oscillatory rheology studies of functional amyloid hydrogels for presenting the storage modulus (G') and loss modulus (G"). FIG. 8B depicts the thixotropic nature of the hydrogels by stress-strain rheological measurement of the functional amyloid hydrogels.

Figure 9:
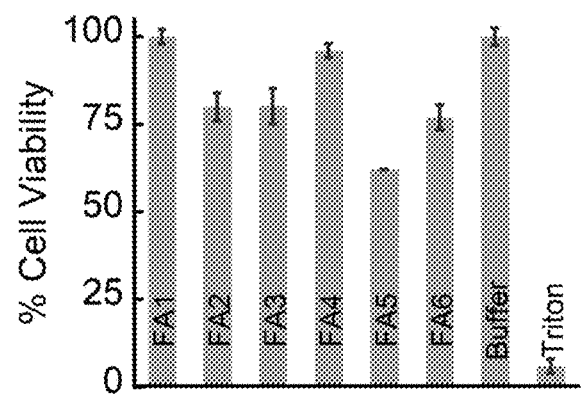

FIG. 9 depicts the MTT assay, which represents the biocompatibility of the functional amyloid hydrogel using SH-SY5Y, neuroblastoma cells.

Figure 10A:
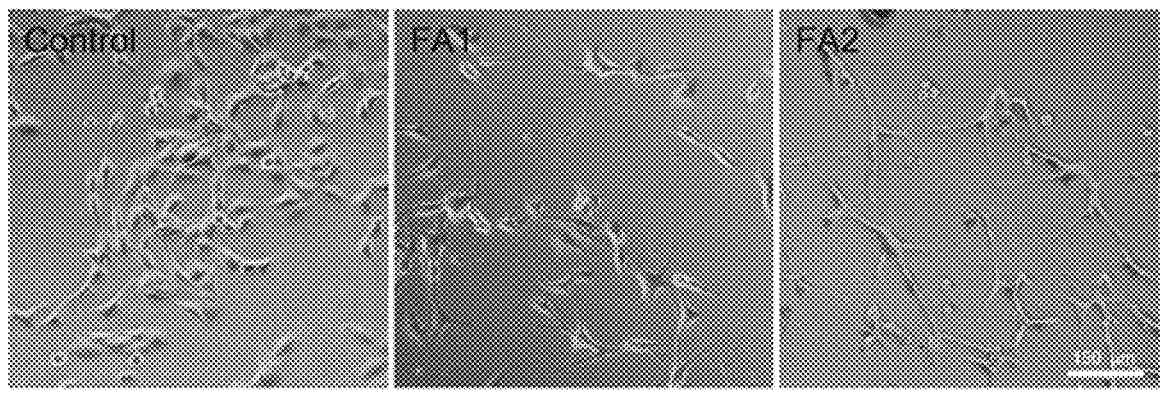
Figure 10B:
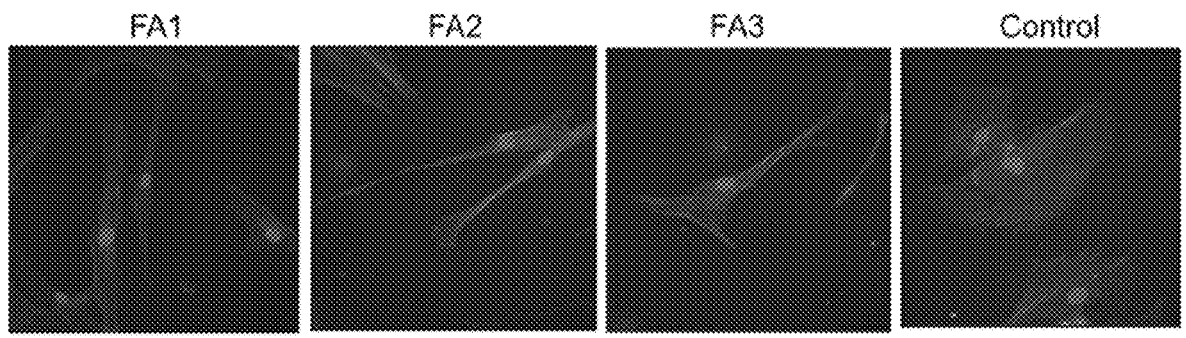
Figure 10C:
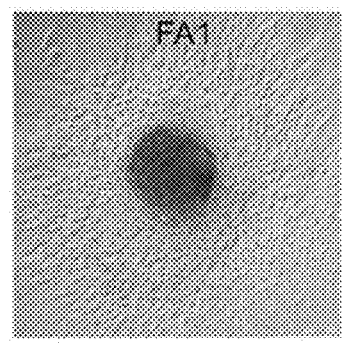
Figure 10D:
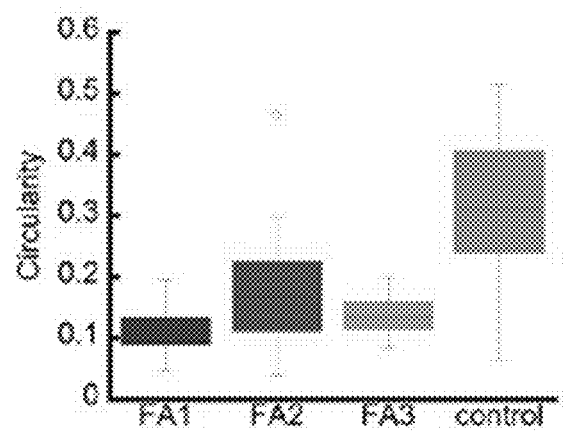
Figure 10E:
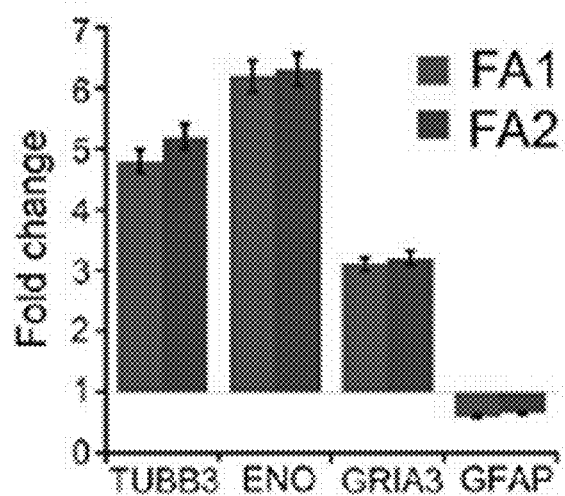

FIGS. 10A, B, C, D and E depicts the role of functional amyloid hydrogels for cell adhesion and differentiation. FIG. 10A shows phase contrast images of SH-SY5Y on glass and designed hydrogels FIG. 10B shows immunocytochemistry of hMSCs as stained with actin. FIG. 10C depicts the phase contrast image of 3D culture of hMSCs on day 7. FIG. 10D. the circularity plot of hMSCs cultured on glass and functional amyloid hydrogel. FIG. 10E represent the gene expression profile of hMSCs after culturing for 7 days on glass and designed hydrogels.

Figure 11:
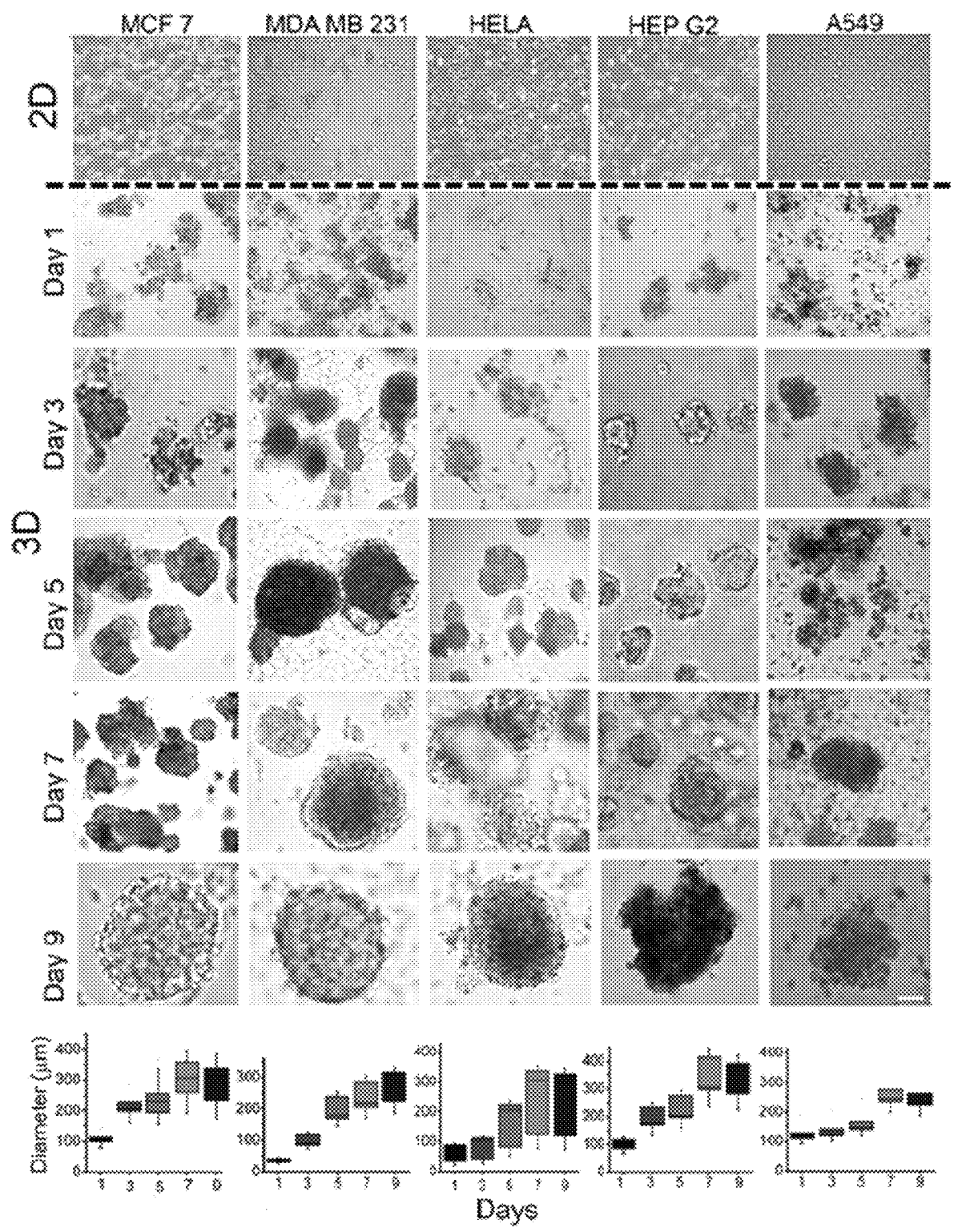

FIG. 11 depicts formation of spheroids/tumoroids and growth kinetics of different cell lines cultured on FA1 hydrogel with course of time through spread method. Phase contrast images of formed spheroid of all the different cell lines of different origin captured every alternate days at 10× magnification, scale bar 100 μm.

FIGS. 12 A, B and C depicts spheroid formation of different cell lines cultured on different class of functional amyloid hydrogels, diameter of spheroids/tumoroids and control after 5 days of incubation. FIG. 12 A shows Phase contrast images of spheroid/tumoroids of different cell lines cultured on different class of hydrogels after 5 days of incubation. FIG. 12 B shows diameter of spheroid/tumoroid of different cell line after 5 days of culture on functional amyloid hydrogels and matrigel served as standard. FIG. 12 C. shows controls for spheroid formation, where MCF 10 A served as cell control and tyr-ala as gel control. Scale bar 100 μm.

Figure 13:
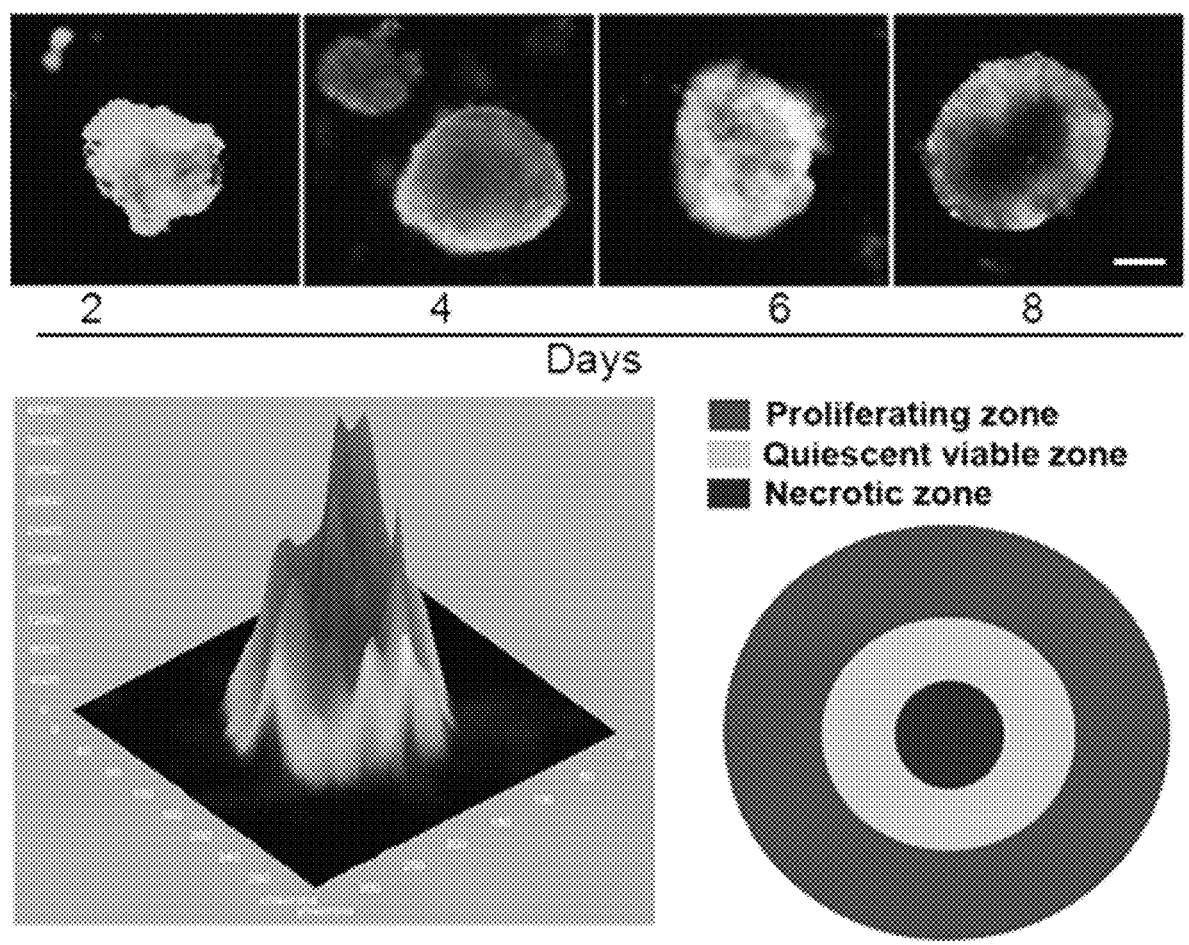

FIG. 13 illustrates cell viability assay of spheroids/tumoroids on different days, using a live/dead staining with ethidium homodimer-1 and calcein-AM. Viable cells appear as green, while non-viable cells appear as red. The $8^{th}$-day-old spheroid had visibly three regions, where densely packed cells at the centre of the spheroid representing necrotic core, mid region representing quiescent viable zone and outermost region is proliferating zone where, cells growing at the periphery, scale bar 100 μm.

Figure 14:
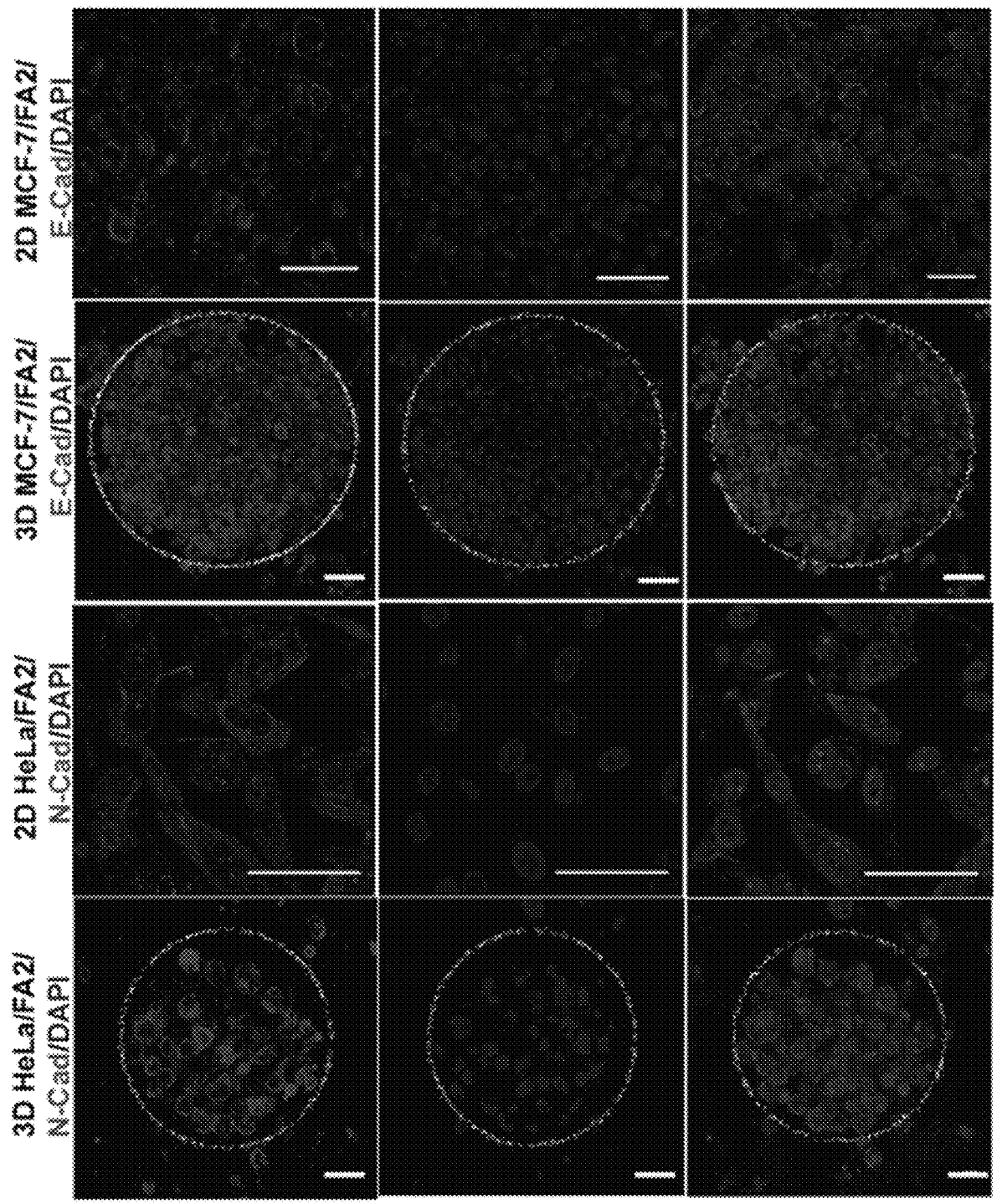

FIG. 14. Cadherin and DAPI staining of spheroids cultured on FA 1 hydrogel through spread method after 5 days of incubation, scale bar 100 μm.

Figure 15:
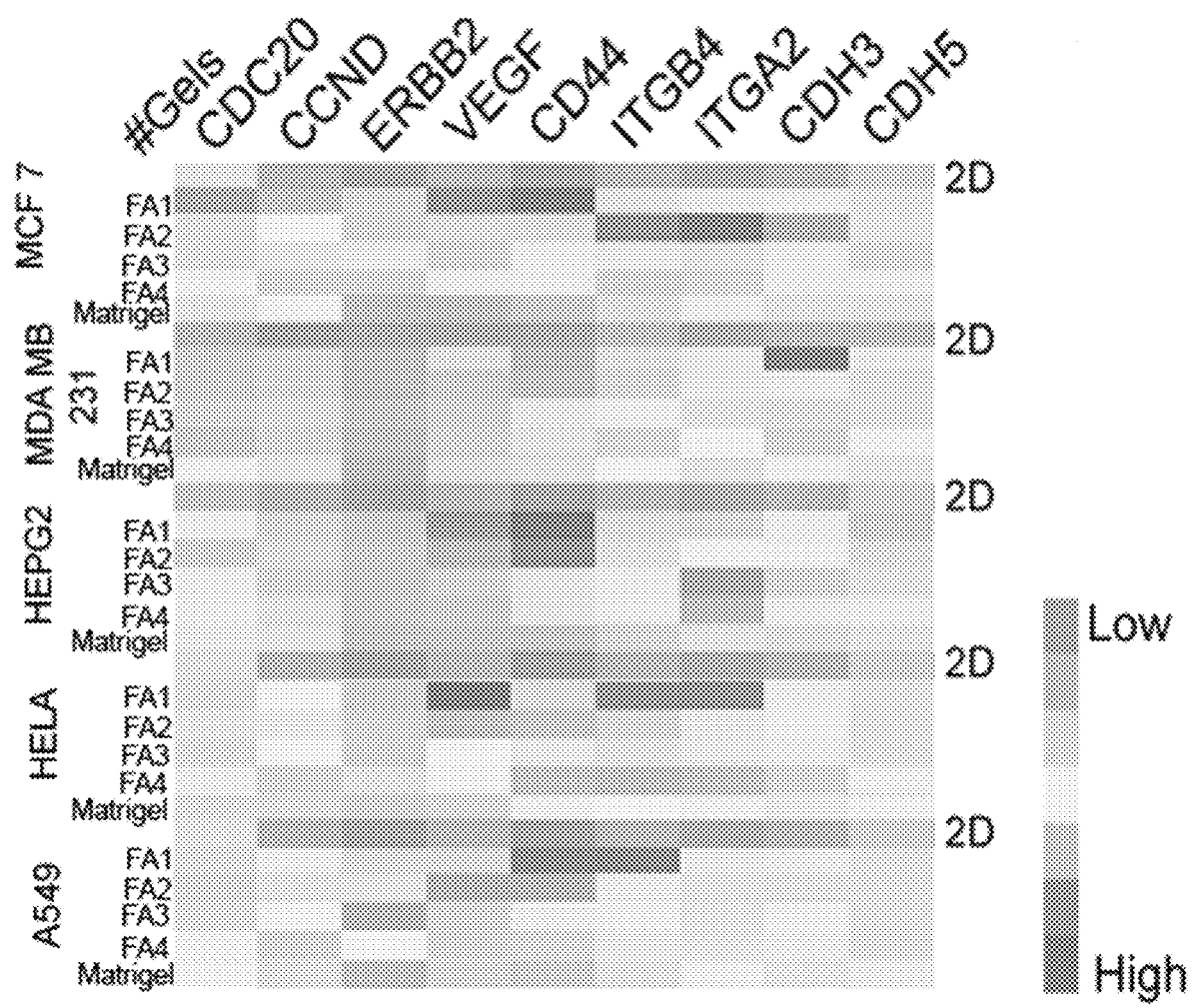

FIG. 15. depicts gene expression profile of spheroids of different cell lines cultured on functional amyloid hydrogels through spread method.

Figure 16:
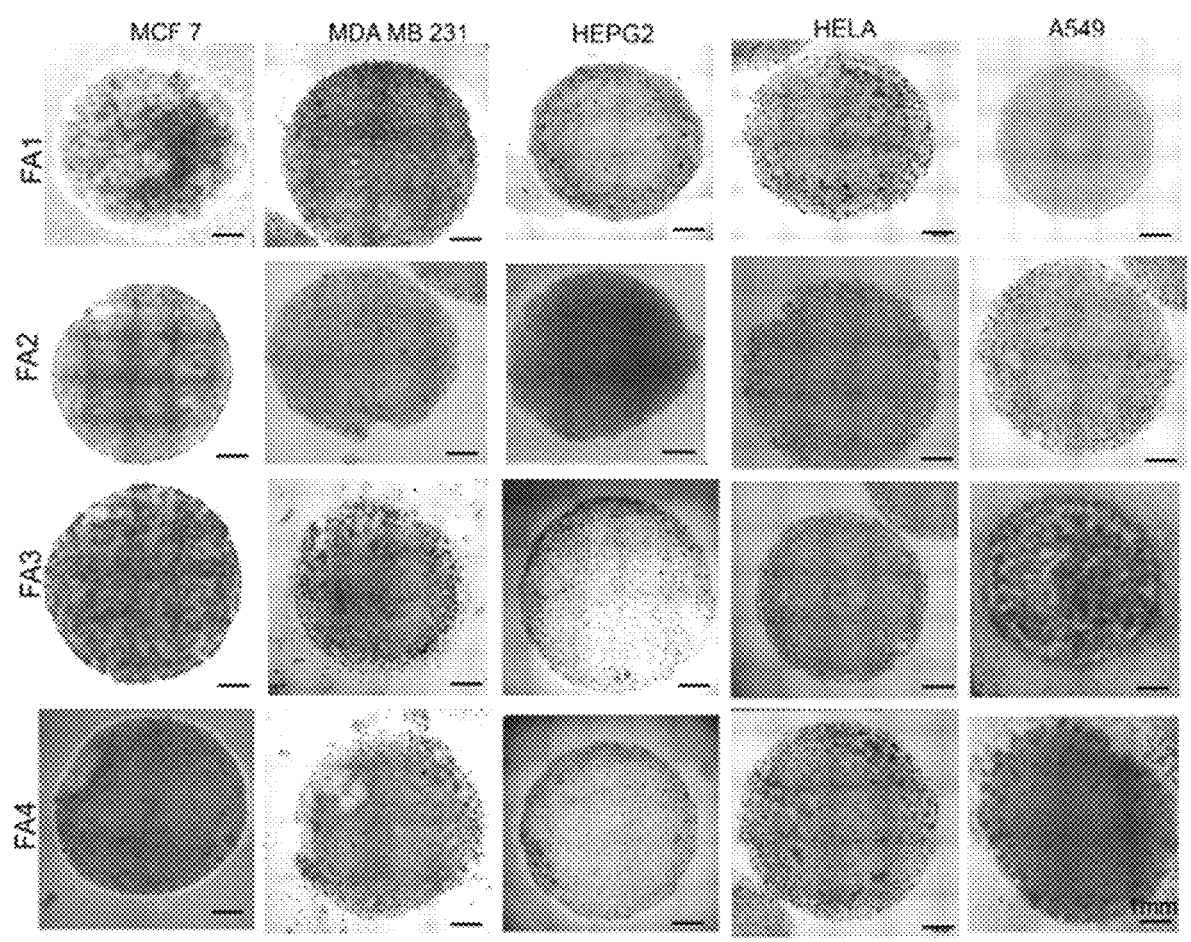

FIG. 16. depicts spheroids/tumoroids of various cell type and origin through drop cast method on series of functional amyloid hydrogel.

Figure 17:
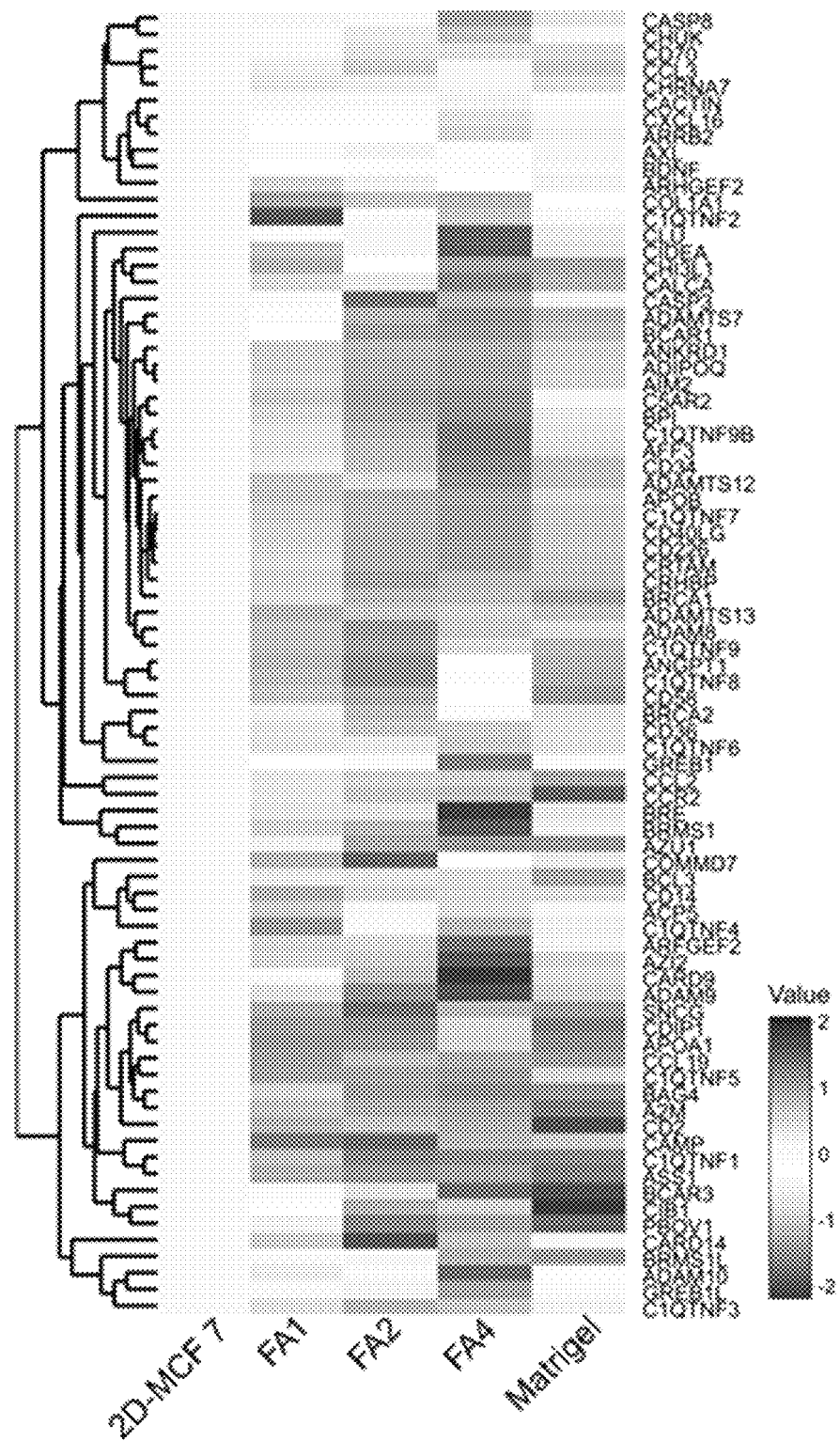

FIG. 17 depicts microarray analysis of cancer genes on generated spheroids compared to cancer cells grown as monolayer or 2D. Matrigel served as control.

Figure 18A:
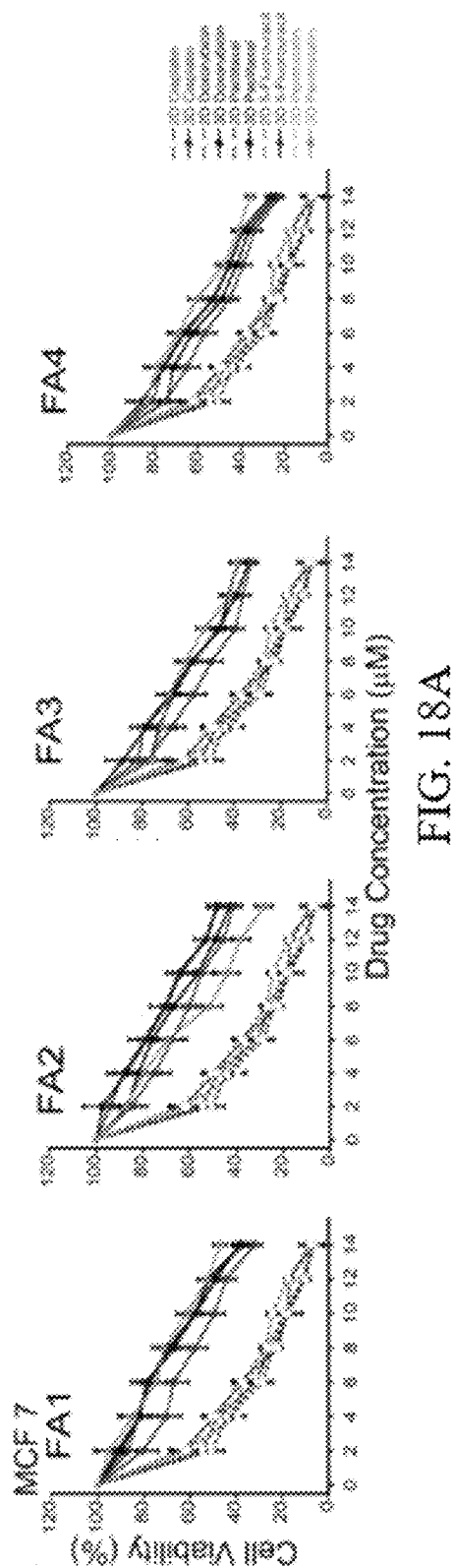
Figure 18B:
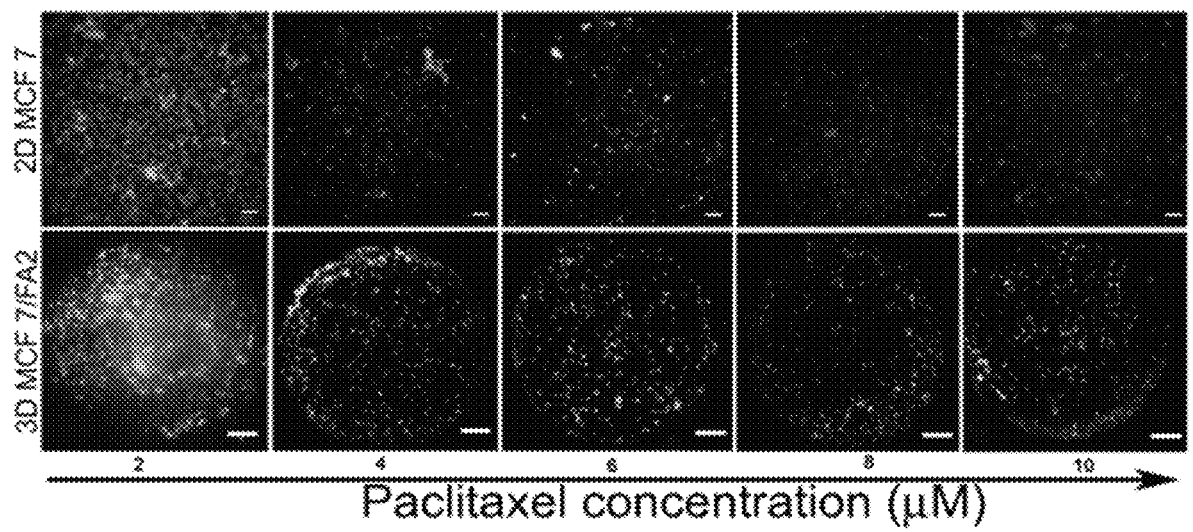
Figure 18C:
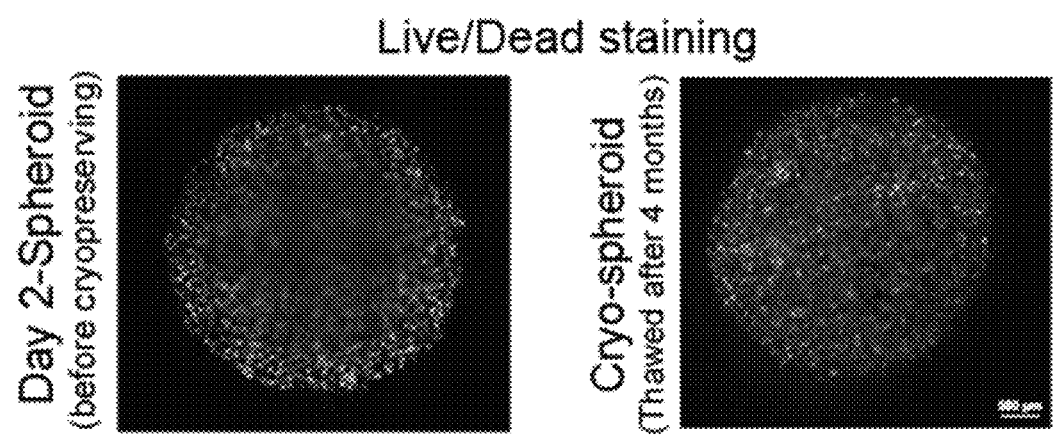

FIG. 18. depicts effect of different anti-cancer drugs on spheroid/tumoroids cultured on functional amyloid hydrogels compared to 2D culture and cryo-spheroids. Data representing cell viability for different dose after 24 h of treatment. FIG. 18A depicts effect of different anti-cancer drug on spheroids through MTT assay. FIG. 18B describes fluorescence study to observe the effect of drug on 2D versus 3D. FIG. 18C depicts live/dead staining of spheroids before and after preservation with calcein-AM and ethidium homodimer-1. Scale bar 500 μm.

FIGS. 19 A, B, C and D illustrates formation of breast cancer tumoroids, viability and effect of anticancer drug. FIG. 19 A. shows formation of breast cancer tumoroids by spread and drop cast method {Left (Scale bar 100 μm) to right panel (Scale bar 500 μm)}. FIG. 19B. shows viability of these tumoroids by calcein AM-ethidium homodimer-1 staining (Left to right panel). FIG. 19C. depicts population of CD44+/CD24− in generated organoid/tumoroid compared to dissected mice tumor. FIG. 19D. depicts effect of anticancer drugs (doxorubicin) on these generated tumoroids after 24 h by flowcytometry based apoptosis detection.

Figure 20A:
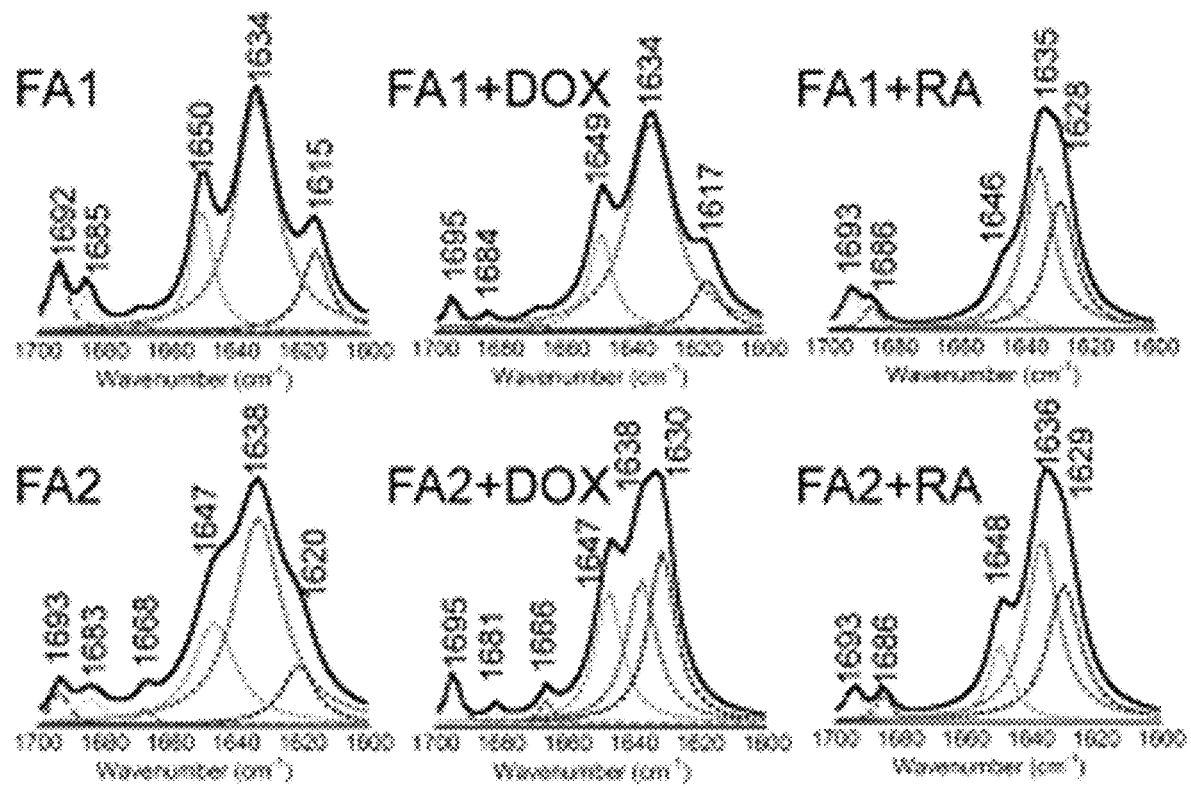
Figure 20B:
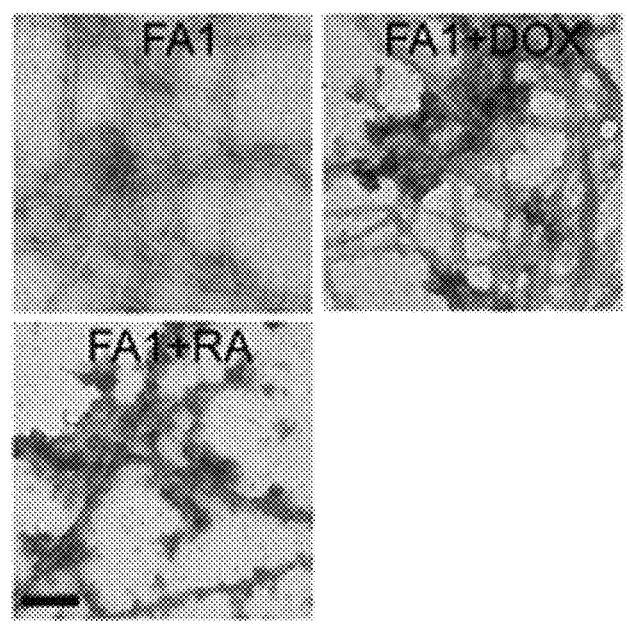

FIGS. 20A and B show encapsulation of drug/protein into the functional amyloid hydrogels. FIG. 20A represents the secondary structural analysis of drug/protein encapsulated in the hydrogels. FIG. 20B depicts the TEM image showing fibril formation leading to hydrogel formation after encapsulation with drug/protein.

Figure 21:
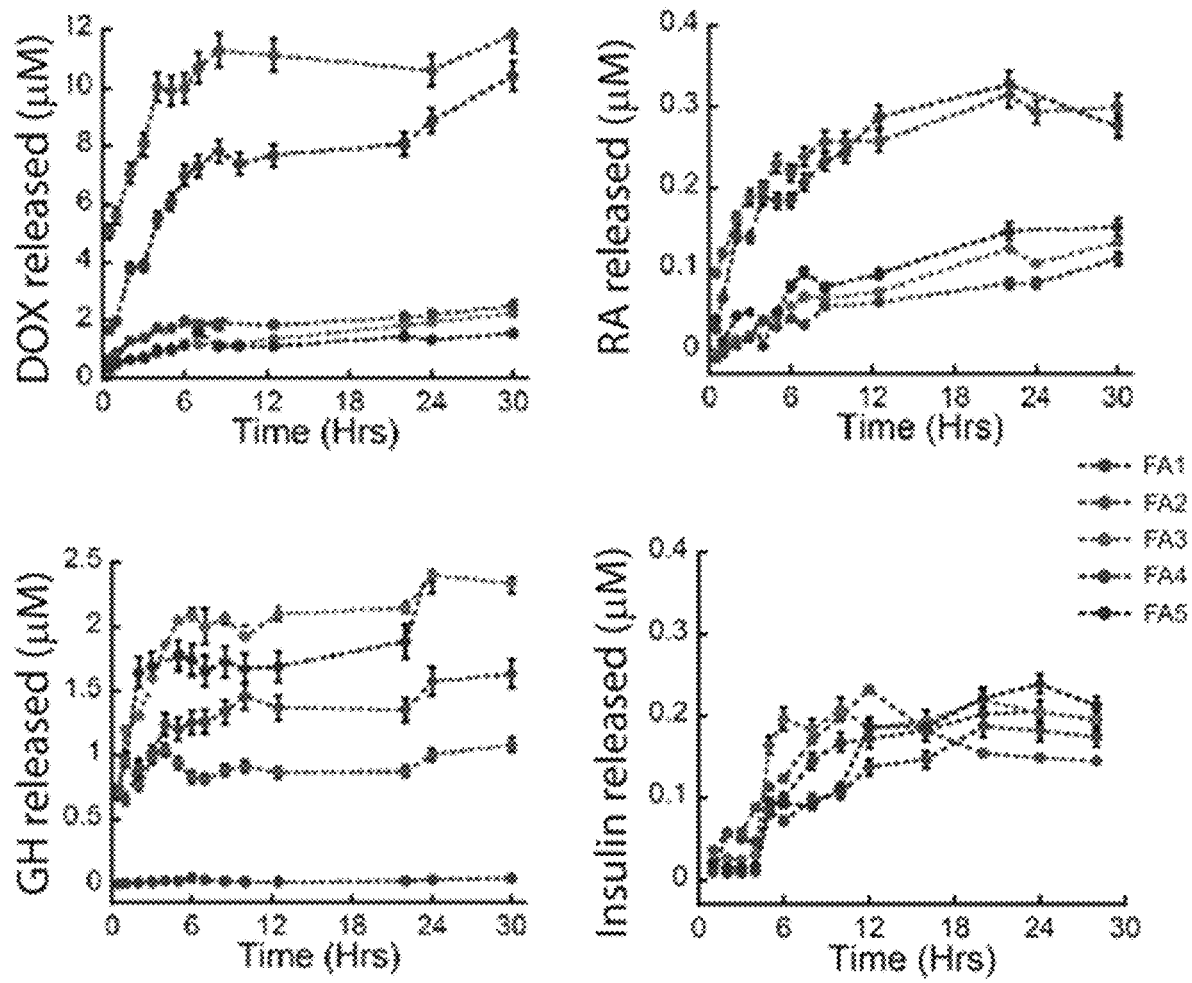

FIG. 21. In vitro release studies of various therapeutic agents from functional amyloid hydrogels over a period of time.

Figure 22A:
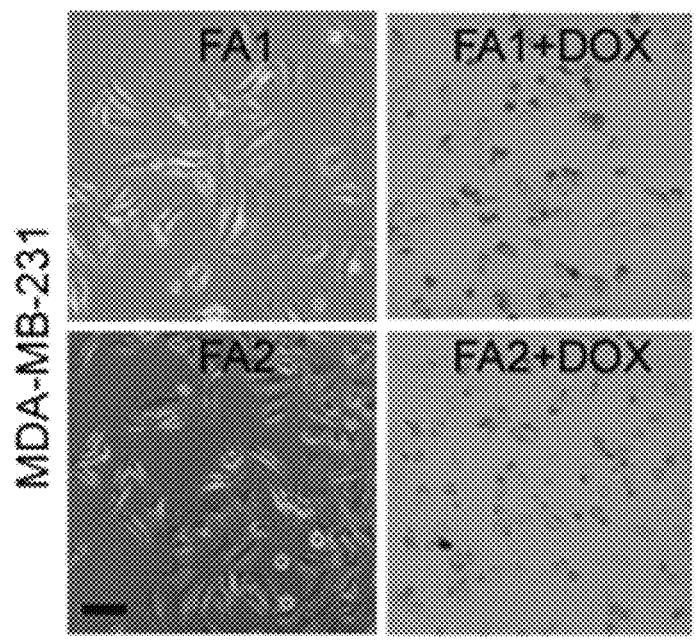
Figure 22B:
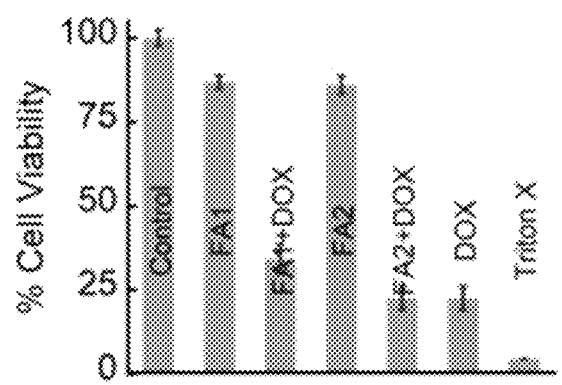
Figure 22C:
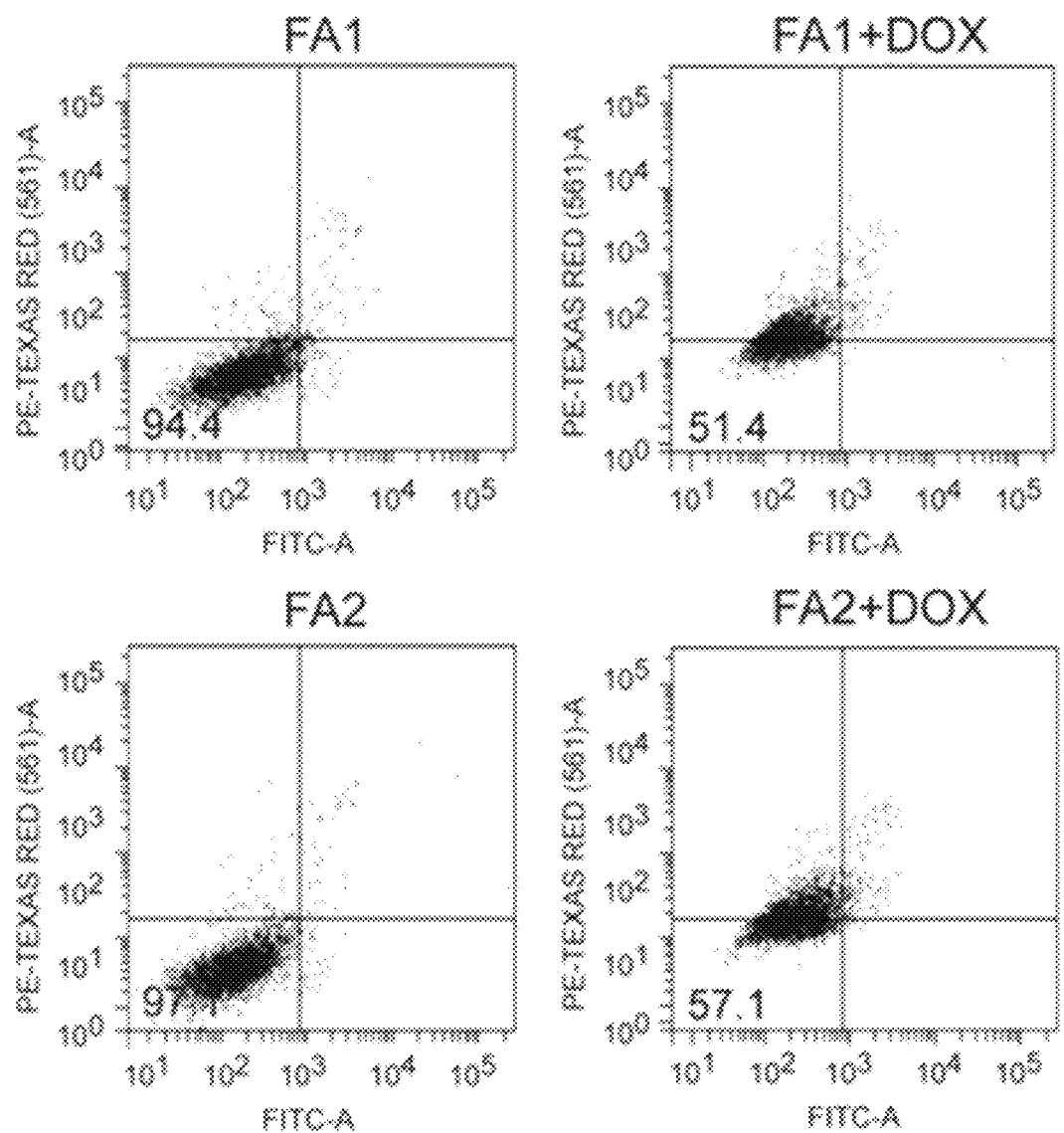

FIGS. 22A, B and C depict the efficacy of the functional amyloid hydrogel for delivering DOX. FIG. 22A shows phase contrast images of MDA-MB-231 cells treated with DOX encapsulated hydrogels. FIG. 22B represents MTT assay showing death in MDA-MB-231 cancerous cells in the presence of DOX encapsulated hydrogels. FIG. 22C depicts apoptosis assay of MDA-MB-231 cells upon treatment with DOX encapsulated hydrogels using FACS analysis.

Figure 23A:
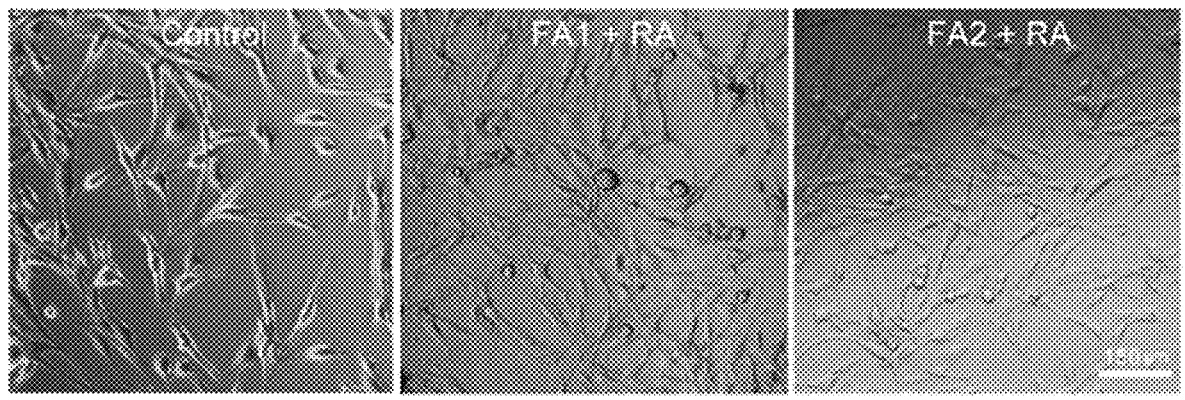
Figure 23B:
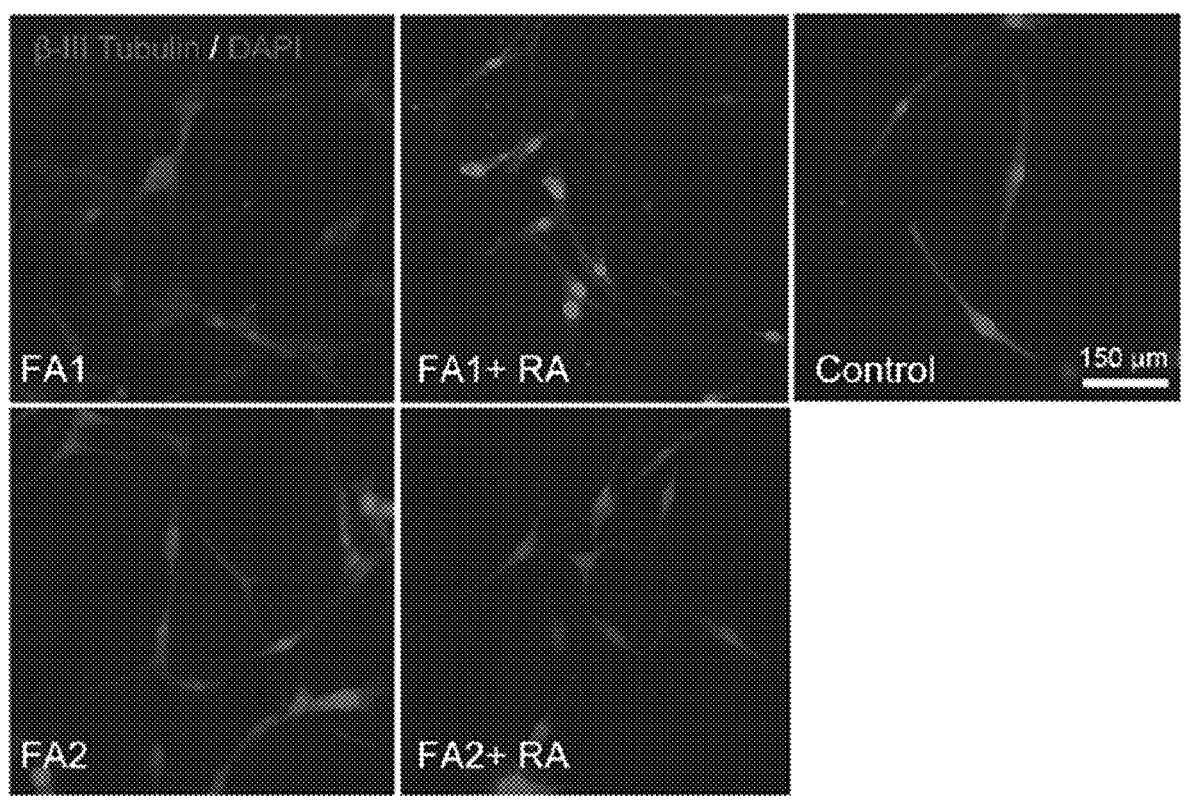
Figure 23C:
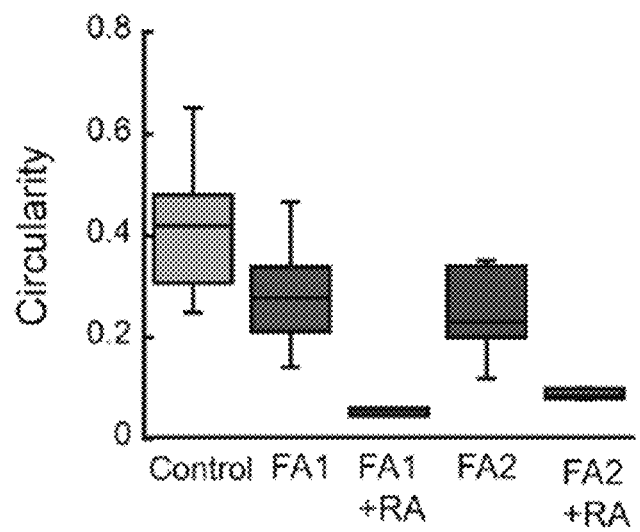
Figure 23D:
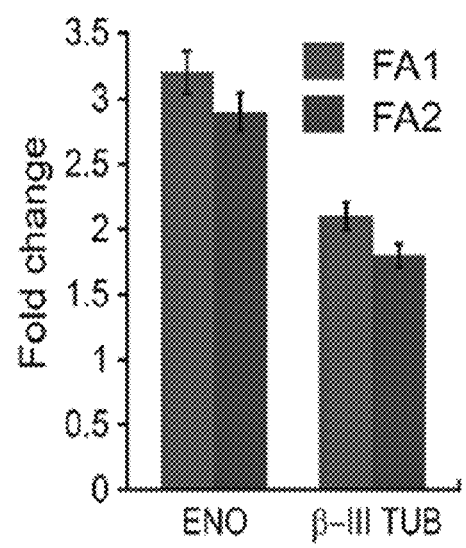

FIGS. 23A, B, C and D show differentiation of SH-SY5Y cells on functional amyloid hydrogels entrapped with RA. FIG. 23A shows phase contrast images of SH-SY5Y cells grown on the hydrogels with and without RA encapsulation. FIG. 23B shows SH-SY5Y cells cultured on the hydrogel only and amyloid containing RA hydrogel for 48 hrs and stained with a neuron-specific marker, β-III tubulin and nucleus are stained with DAPI. FIG. 23C represents the cell circularity plot of SH-SY5Y cells grown on various designed hydrogels. FIG. 23D represents the gene expression profile of SH-SY5Y after culturing for 5 days on glass and designed hydrogels.

Figure 24A:
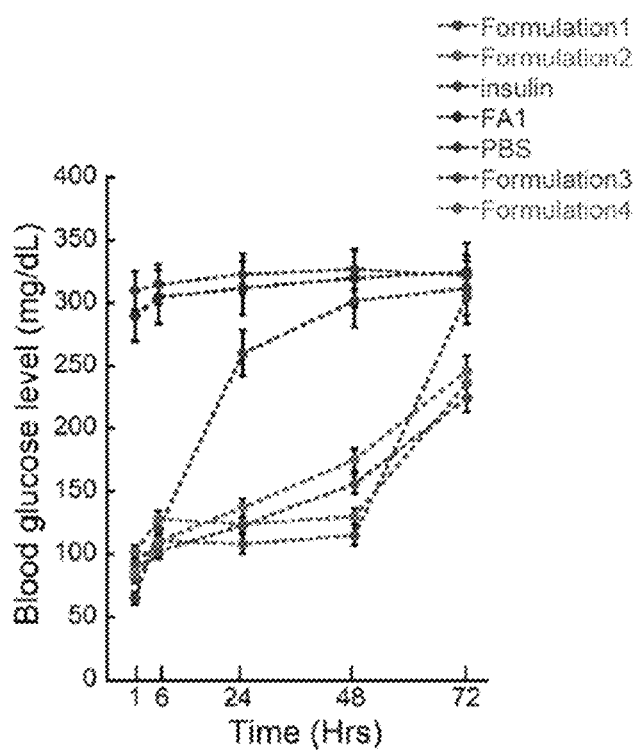
Figure 24B:
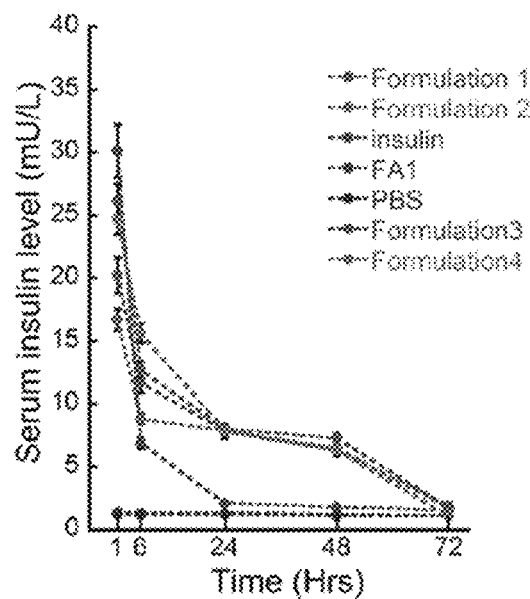

FIGS. 24A and B show the efficacy of the designed hydrogels as insulin delivery vehicles in diabetic rat model. FIG. 24A depicts the blood glucose level of the diabetic animals after treatment with insulin encapsulated hydrogels. FIG. 24B. show the serum insulin levels of the animals after treatment with insulin encapsulated hydrogels.

Figure 25:
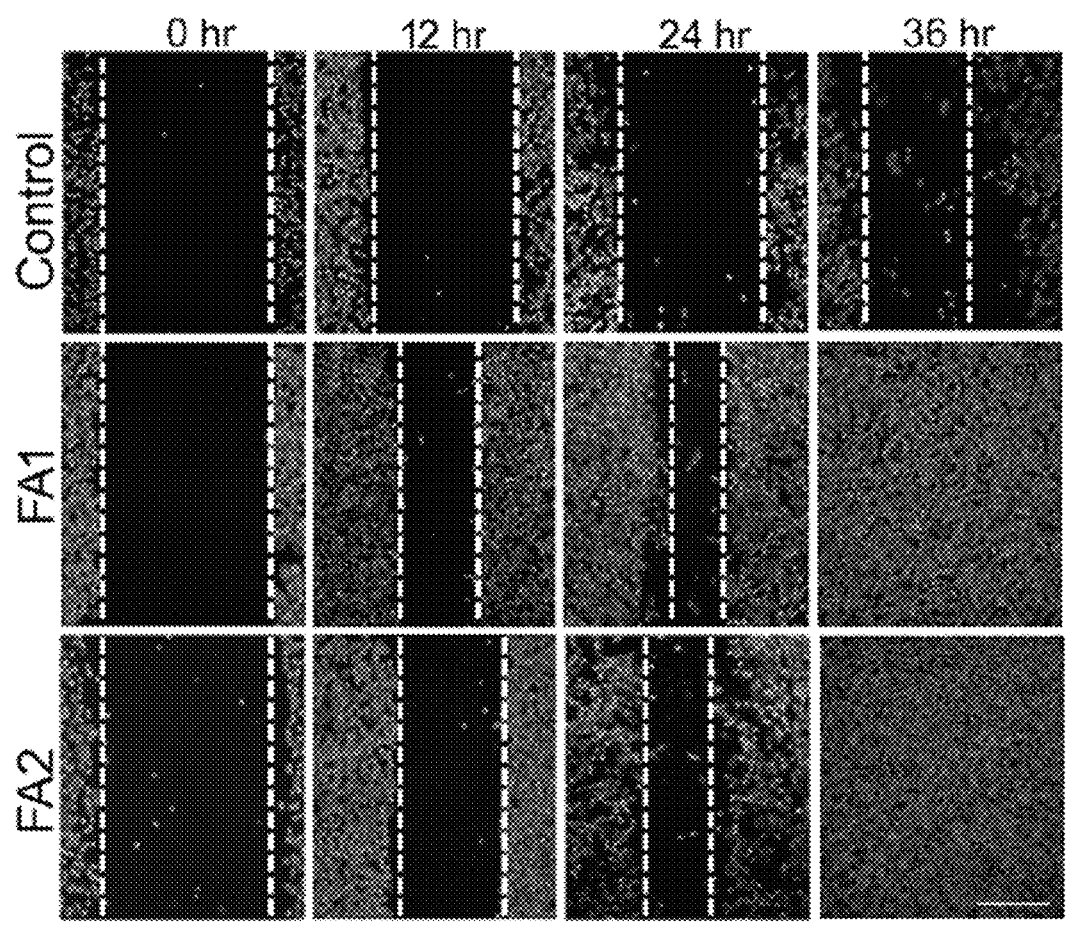

FIG. 25 depicts in vitro scratch assays of L929 dermal fibroblast cells treated with PBS as control, functional amyloid hydrogels with and without bFGF-2.

DETAILED DESCRIPTION OF THE INVENTION

The invention herein describes novel functional amyloid hydrogels, which self-assembles to form a three-dimensional nanofibril matrix and their applications, but not limited to cell adhesion, tissue engineering, tumoroid development, drug delivery and wound healing.

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof. Also, expressions such as "at least one of," when preceding a list of elements, modify the entire list of elements and do not modify the individual elements of the list.

The present invention provides the design of peptide-based self-assemble hydrogelators developed from functional amyloids with optimum stiffness, whose side chains can be easily modified and inexpensively synthesized and can mimic the extracellular matrix. According to the present invention, the nanofibril matrix is primarily made up of peptide sequences made by few amino acids. The present invention further elaborates on the method of using the hydrogels as a scaffold for cell adhesion and tissue engineering purposes.

The present invention further describes the method of developing 3D tumor models from various cancerous cell lines using the functional amyloid hydrogels and evaluating the utility of these hydrogels to test the efficiency of anti-cancer drug therapeutics on the developed 3D tumor models.

Also, the present invention pertains to the development of functional amyloid hydrogelators for delivering therapeutic agents. It also relates to the method of using these hydrogels for delivering active biological agents by encapsulating the same in it and exhibiting a controlled and sustained release of the biologic agent.

The present invention describes the method of development of functional amyloid hydrogels as wound healer capable of inducing cell proliferation and cell migration.

Self-Assembly Peptides and their Characteristics

In one aspect, the present invention describes a peptide-based self-assemble hydrogelators from functional amyloids that employs small peptides as the gel scaffold building block. Peptides may be designed having highest β-aggregation prone region from functional amyloid sequences such that they undergo gelation only after intermolecular folding into a cross-beta-sheet conformation that is capable of intermolecular association. The folding event can be triggered by biological compatible cues, for example pH, temperature, and salt or specific ion concentration affording responsive hydrogelation systems. Using peptides is advantageous as they can be quickly synthesized and it is possible to substitute residues for tailored material and biological properties. The hydrogel formation involves self-assembly therefore does not require exogenous cross-linking agents. This hydrogelation strategy will result in a cyto-compatible gelation system capable of mimicking extracellular matrices that may be used for various potential applications such as cell adhesion, tissue engineering, tumoroid model, drug delivery and other in vitro and in vivo constructs. The present invention builds a relationship between the structure of the peptide and ultimately hydrogel formation, their morphological, rheological properties, and cellular interactions.

The present invention utilizes majorly four fundamental attributes for designing peptide to form hydrogels: 1) Small stretch of amino acids exhibiting beta-aggregation propensity may be used to prepare hydrogels. 2) Self-assembly interactions majorly contribute to hydrogel formation thereby eliminating the need of external cross-linking agents. 3) The self-assembly of peptides leading to hydrogel formation may not occur unless a targeted conformation is achieved. 4) The supramolecular assembly resulting in hydrogelation, can be induced by specific environmental stimuli.

Physically cross-linked self-assembled hydrogel networks are responsive to mechanical stimuli. This attributes a free flowing suspension after applying shear force and subsequent self-healing of the gel network after cessation of the stimuli.

The present invention relates to functional amyloid hydrogels comprising of functional amyloid nano-fibril peptides. Examples of peptides that may be used in one or more aspects of the present invention include sequences selected from the group consisting of

FA1
KLMEI (SEQ ID: 1)

FA2
KLLDI (SEQ ID: 2)

FA3
AVVLS (SEQ ID: 3)

FA4
FVQWL (SEQ ID: 4)

FA5
NLLFN (SEQ ID: 5)

FA6
LVTLF (SEQ ID: 6)

The nano-fibril peptides are derived from non-toxic amyloid protein sequences. The functional amyloid nano-fibril peptides are not limited to the sequences as disclosed and can also include other functional amyloid nano-fibril formed by various peptide/protein sequences.

The functional amyloid hydrogels as provided herein are derived from functional amyloid nano-fibril peptides, wherein one end of said peptides is Fmoc capped.

The present invention also discloses functional amyloid hydrogels with various applications and the method of their preparation comprises the following steps:
a. designing stretch of amino acids from functional amyloid proteins but not limited to it;
b. modifying the selected peptides by N-terminal end capping with Fmoc moiety;
c. making a solution of the N-terminal modified peptides;
d. For pH responsive gels (For example FA1): the pH of the peptide solution was modulated to obtain the condition for hydrogelation;
e. For temperature responsive gels (For example FA4), the temperature of the peptide solution was altered with multiple cycles for obtaining hydrogels.
f. For altering the rigidity of the hydrogels varying concentration of salt (example, NaCl) was used (range: 0-300 mM) for its suitability as a platform for various biological applications.

In one implementation, a method of preparing the hydrogels comprises the steps of
a. preparing a solution comprising peptide having sequences selected from the group consisting of KLMEI, KLLDI, AVVLS, FVQWL, and NLLFN and LVTLF;
b. altering one or more chemical or physical characteristic of the solution, to obtain a hydrogel, wherein the characteristic is selected from a group comprising temperature, pH and ionic strength.

The peptide sequences are selected using an algorithm TANGO that predicts the most amyloidogenic segments from non-toxic amyloids forming peptides. The peptide sequence was further modified with the addition and substitution of other amino acids to create more peptides along with Fmoc protection at the N-terminus.

The selected individual peptides are dissolved in a buffer at pH 7.4 and the pH is increased till the peptides dissolve to form a clear solution. On dissolution, the pH of the solution is brought back to physiological pH 7.4 and 0-300 mM NaCl is added. The gel solution is left undisturbed at room temperature for 5 to 15 mins to form a hydrogel.

The present invention further discloses functional amyloid hydrogels obtained by the method as described herein.

The gelation of these peptides was tested using the gel inversion test. The morphological characterization of the hydrogels was determined using AFM and TEM, which revealed a nano-fibrillar structure. The secondary structure of the hydrogels was tested using FTIR. The results from both the study showed that the designed hydrogels contained the presence of β-sheet rich structures. Further, the nature of gel fibrils was found to be amyloidogenic using Thioflavin T and Congo red binding assay. The mechanical strength of the hydrogels was studied using oscillatory rheology and the thixotropic property of the hydrogel was confirmed using stress-strain rheology. Further, the hydrogels were used for cell adhesion, tissue engineering, three-dimensional tumor model development, drug delivery and wound healing studies.

The present invention describes novel hydrogels and their design from amyloidogenic proteins/peptides, which form non-toxic amyloid fibrils that constitute the hydrogel. In addition, functional amyloid hydrogel also describes hydrogel from stretch of amino acids from functional amyloid forming proteins. As used herein, functional amyloid hydrogel describes hydrogel amyloid fibrils by from protein or peptide with no cytotoxicity. The present invention also describes a method of preparing the hydrogels by altering one or more chemical or physical characteristics of the solution, which includes, but are not limited to pH, temperature, organic solvents and salt concentration.

In one particular embodiment, any peptide may be designed from non-toxic amyloid sequences comprising a cross-beta sheet structure, which can self-assemble to form a three-dimensional network and consequently a hydrogel in response to one or more environmental signals. Also, the porosity of the designed hydrogel can be modulated by adjusting the salt concentration. In another object of the invention, the hydrogel shows good tensile strength and optical transparency.

In one aspect, the amount of weight of peptide and/or salt concentration may be varied to form a hydrogel with desired stiffness. Hydrogel mentioned in the present invention have a modulus of about 500 Pa to about 1000 Pa, from about 1000 Pa to 10000 Pa. In another aspect the hydrogels formed are thixotropic in nature and enables easy encapsulation of but not limited to cells, drugs, small molecules, peptides, proteins and other biological agents.

In one embodiment, the designed hydrogels as described in the present invention are completely non cytotoxic in nature and induces the adhesion, proliferation and differentiation of mammalian cells (neuroblastoma) and stem cells.

In one embodiment, hydrogels disclosed in the invention may be used for tissue engineering application. For example, the hydrogels containing cells may be uniformly distributed in the system and aid in cell adhesion, facilitates cell proliferation and differentiation in a lineage specific manner. It may also be used as tissues to replace damaged tissues.

In some embodiments, the hydrogels of the invention have the characteristics of undergoing reversible gelation, wherein one set of conditions hydrogelation takes place and on altering the conditions it forms solution and again reverts back to gel form on changing the conditions. This attribute of the hydrogels of the invention may be used in various applications such as tissue engineering, three-dimensional tumoroid model, drug delivery and wound healing. In some aspects, these hydrogel as mentioned in the invention may be readily functionalized with growth factors or therapeutics further optimization in accordance to a particular application. Thus, hydrogels of the invention may consist of additional components, which may be peptides, chemical or other biological agents that give the hydrogels of the invention varying characteristics.

In some of the aspects of the present invention, the generated hydrogels mimic extracellular matrix and thereof support cell growth and proliferation. In another aspect, the generated hydrogels even in the absence of any cell binding and/or cell adhesion motifs (For example; RGD) support adhesion and proliferation, independent of cell type.

The present invention encompasses embodiments of functional amyloid hydrogels as a scaffold for spheroid/tumoroid development. In one of the aspects, presently described scaffolds induce cells of any type or origin to form tight aggregates as spheroid/tumoroids similar to in vivo tumor which are capable of mimicking tumor microenvironment and architecture. In another aspect, the generated tumoroids showed higher resistance to anticancer drugs compared to the same cells when cultured as monolayers or 2D.

In one of the aspects, functional amyloid hydrogel support breast tumor collected from mice to form tumoroids/organoid and showed even more resistance to anticancer drugs than same tumor cells cultured as a 2D monolayer. Hence, the hydrogel mentioned in the disclosure provide an excellent platform to generate tumoroids/spheroids from but not limited to cancer cell lines and mice tumor. In another embodiment, this platform can be used to generate patient centric organoid model from cancer biopsies and/or tissue sample, screening of anticancer compounds, repurposing of existing drugs, healthcare devices and thereby aid in the development of precision medicine and personalized medicine.

In one aspect, hydrogel of the present invention provides an absorbable and locally implantable drug delivery vehicle for controlled and sustained release of the biological agents encapsulated within. These are easy to synthesize process and fabricate. In another aspect, the present invention provides a method of delivering a therapeutic agent to an animal in need thereof, comprising administering a hydrogel encapsulating the therapeutic agent and one or more peptides to the animal such a method may be practiced on any type of animal. Any other biological agent known to those skilled in the art can also be employed, for example, small molecules, peptides, proteins and other biological agents. In another preferred embodiment, the hydrogel of the invention can release the therapeutic agent in a controlled manner over a period of time of at least three days, preferably at least 7 days and more preferably at least 14 days.

In another aspect the present invention discloses nontoxic amyloid nanofibrils hydrogel as wound healer capable of inducing cell proliferation and migration. The hydrogel material of the invention may optionally contain any and/or antimicrobial, and/or, antifungal and/or antibacterial and/or bacteriostatic agent and/or organic additives may be added.

Uses of Self-Assembled Peptide Scaffolds

In another aspect, the present invention further elaborates on the method of using the hydrogels as a scaffold for cell adhesion, tissue engineering purposes. The present invention further describes the method of developing 3D tumor models from various cancerous cell lines using the functional amyloid hydrogels and evaluating the utility of these hydrogels to test the efficiency of anticancer drug therapeutics on the developed 3D tumor models.

Also, the present invention pertains to the development of functional amyloid hydrogelators for delivering therapeutic agents. It also relates to the method of using these hydrogels for delivering active biological agents by encapsulating the same in it and exhibiting a controlled and sustained release of the biological agent. Moreover, the present invention also describes application of these hydrogels in promoting wound healing.

Functional Amyloid Hydrogel for Cell Adhesion and Tissue Engineering Applications The interactions between cell and matrix play a pivotal role in cell adhesion, proliferation and cell differentiation. Lately, the development of scaffolds that can mimic and substitute extracellular matrix is the area of focus in the field of tissue engineering. The materials employed in the development of scaffolds are derived from both natural and chemical origin. Therefore, biodegradability and immunogenicity still remains a concern for biomaterials derived from chemical sources. The cells may adhere readily to scaffolds developed from natural derivatives, but it may lead to undesirable contamination issues and immunogenic response, as they are isolated from animals. Amyloid fibrils mimic extracellular matrix and can thus support cell adhesion and proliferation of any cell type. Moreover, cells adhere to amyloid fibrils in the absence of any cell binding or cell adhesion motif (for example RGD motif). Hence, functional amyloid hydrogels may serve as a biomaterial for cell adhesion overcoming the above mentioned drawbacks of other scaffold system.

To assess the suitability of the functional amyloid hydrogels as biomaterials for cell adhesion, proliferation and differentiation, initial experiments of cell attachment and spreading on the surface of the gels via 2D and 3D culture was performed using SH-SY5Y, neuroblastoma cell line and hMSCs. The cells adhered to different hydrogels and the difference was noticeable in spreading area and cell shape. Further, differentiation of hMSCs towards neuronal lineage was studied by gene expression profiling. The neuronal markers GRIA3, TUBB3 and ENO were up-regulated in cells grown in presence of hydrogels and GFAP was down-regulated.

In one embodiment, the present invention provides a method for developing a scaffold for cell adhesion, the method comprising growing of cells on the functional amyloid hydrogels as described herein.

The present invention provides a method for developing functional amyloid hydrogels and using the same as a scaffold for cell adhesion and differentiation, comprises the steps of:
(a) Designing and preparation of the functional amyloid hydrogels
(b) Testing gelation of the hydrogels by the gel inversion test
(c) Determining the biocompatibility of the hydrogels
(d) Cell adhesion studies by 2D cell culture of SH-SY5Y and hMSC using functional amyloid hydrogels
(e) The 3D cell culture of hMSC on these functional amyloid hydrogels
(f) Immunostaining for β-II tubulin and actin expression in 2D cell culture of SH-SY5Y and hMSC using these hydrogels
(g) Gene expression analysis for neuron-specific markers (GRIA3, GFAP, TUBB3 and ENO) in 2D cell culture of hMSCs Functional Amyloid Hydrogel for Organoids, Spheroids and 3D Cell Culture The present invention also discloses functional amyloid hydrogel as three-dimensional cultural scaffolds capable of mimicking extracellular matrix. These porous nanofiber matrix results in a three-dimensional cell culture composition that provides support for robust, accessible and high-throughput screening tissue models similar to in vivo tumor model. The presently described hydrogel maintains and support cell morphology, heterogeneous cell types and populations, cell-cell and cell-matrix interactions.

In one embodiment, the present invention provides a method for developing spheroids and/or tumoroid for use as 3-dimensional tumor models, the method comprising:
a. dissolving the functional amyloid hydrogels as described herein to obtain a solution of the hydrogel;
b. mixing the solution of the hydrogel with cells and incubating the cell-hydrogel mixture; and
c. culturing the mixture containing solidified hydrogel in a suitable medium to obtain the spheroids and/or tumoroid.

In one embodiment, the cells are selected from cancerous and tumour cells selected from human breast cancer cells, lung cancer cells, cervical cancer and liver cancer cells.

The cells can also be selected from a population of cells isolated from an animal tumor and not incubated in cell culture medium before contact with the hydrogel.

The present invention describes a method for developing spheroids for use as three-dimensional tumor models, the method comprising:
(a) Designing and preparation of the functional amyloid hydrogels
(b) Testing gelation of the hydrogels by the gel inversion test
(c) Determining the biocompatibility of the hydrogels
(d) Dissolving the functional amyloid hydrogels as provided herein to obtain a solution of the hydrogel;
(e) Mixing the solution of the hydrogel with cells and spreading the cell-hydrogel mixture on hydrogel coated surface termed as spread method
(f) Culturing the mixture containing solidified hydrogel in a suitable medium to obtain the spheroids.
(g) Characterization of tumor formed from different cancerous cell line with various functional amyloid hydrogels.
(h) Investigation of the expression profile of cancer biomarkers in 3D versus 2D culture.
(i) Maintenance of homogeneity in spheroids for drug testing, mixing the solution of the hydrogel with cells and casted in the form of sphere/drop on hydrogel coated surface termed as dropcast method.
(f) Culturing the mixture containing solidified hydrogel in a suitable medium to obtain the spheroids.
(i) Evaluation of the anti-cancer therapeutics on these spheroids.
(j) Evaluation and characterization of breast tumoroids, cell viability and gene expression analysis cultured in these hydrogels.
(k) Testing of anti-cancer therapeutics on these tumoroids.

As used herein, the terms "cancer," "cancer cells," "tumor," and "tumor cells" (used interchangeably) refer to the cells which show comparatively autonomous growth thereby exhibit an aberrant growth phenotype characterized by cell proliferation control.

The cells used in the method for developing spheroids can be selected from any cancerous cell line. The cells used for the developing the spheroids are selected from a group, but not limited to, consisting of MCF-7, HepG2, HeLa, A549 and MDAMB 231.

The cells before mixing with the hydrogel solution are trypsinized using 1× trypsin-EDTA and pelleted. The cell pellets were mixed with the hydrogel solution. The ratio of cells to hydrogel was determined empirically such that cells are in close proximity to each other. The mixture was then spread over the hydrogel coated cover slip and incubated for 10 minutes for the hydrogel to solidify partially. Subsequently, spread cell-hydrogel mixture was covered with suitable medium and incubated in under standard conditions (37° C., 5% CO2, 95% humidity). In another method the cell-hydrogel mixture was drop-casted to form spheroids. Dulbecco's Modified Eagle Medium (DMEM) supplemented with 10% heat-inactivated fetal bovine serum) was used as growth medium. Other culture mediums are minimal essential media (MEM), RPMI 1640. The culture was maintained for 10 days for spheroid formation.

Culturing of cancerous cells on these scaffolds indicated the formation of spheroids in a few days. Images indicated that initially dispersed cells come closer to form loose aggregates, which later resulted into mature spheroids. Size of spheroid varies from 50-500 µm on the 7th day of culture.

In one embodiment, the diameter range of spheroids is from 50-500 µm.

Subsequently, calcein-AM and ethidium homodimer-1 staining showed cells were viable. To elucidate the cell-cell interaction, the cadherin expression was determined using Western blot and immunofluorescence. Cadherin was found to be up-regulated demonstrating cell-cell interaction to increase during spheroid formation.

For better understanding of effect of the anticancer drug, a drop cast method was adopted for maintaining homogeneity in the size of spheroids. Cells became denser and bigger with following days (size 0.5 mm to 2.5 mm). After 3 days of growth, the border of the spheroids became ruffled indicates cell proliferation mostly at the spheroid periphery. Estimation of number of viable cells in spheroid indicated greater doubling times in spheroid culture versus monolayer cultures.

Various anticancer drugs were tested on these spheroids. Data indicated that $IC_{50}$ values for 2D cultures were approximately half of 3D. Hence, higher cytotoxicity was observed for the same drug in 2D than in 3D models further emphasizing the need of 3D models for drug testing before trials. Therefore, drug testing in 2D does not give the optimal required drug dosage. Spheroids were tested for cryopreservation for biobanking facilities, thus stored in liquid nitrogen for four months in cryoprotectant (10% DMSO). Further, these spheroids were thawed and tested for viability with live/dead assay kit. Results indicated that these spheroids can be cryopreserved and can be utilized for any kind of analysis such as drug testing.

To analyze the organoid/tumoroid formation, primary tumor cells isolated from breast cancer induced mice were cultured on these gels and observed for organoid/tumoroid generation. Tumor were isolated and cultured using our hydrogel as extracellular matrix support in breast culture organoid media through spread and drop-cast method and monitored for days. The images indicated that this hydrogel was reliable scaffold for generation of tumoroid/organoid.

The present invention describes the methods for screening anti-cancer treatment efficacy using functional amyloid hydrogel where non-toxic amyloid hydrogel is seeded with cancer cells and incubated to form spheroids/tumoroid, and the efficacies of anticancer drugs are tested for a given period of time. Population of dead and live cells is estimated and the efficacy of the drug is determined. The presently described scaffold and method for tumoroid generation can be used as healthcare device for high throughput screening of anticancer drugs and personalized medicine.

More particularly, the present invention aids in the development of 3D in vitro tumoroid model of any cancerous cell line on these novel self-assembling classes of hydrogels as a scaffold for testing anticancer therapeutics. Functional amyloid hydrogel as a scaffold for three-dimensional culture provides a realistic and controllable environment for the incorporation of any cancer cells and other biochemical cues to better simulate the native tumor microenvironment. These models serve as more reliable platforms for generating results that would be more identical to in vivo evaluation of chemotherapeutic agents and their delivery systems. The present invention provides physical and structural support for the formation of a 'natural' setting that better recapitulates cell behavior in vivo. It is easy-to-use, inexpensive, and scalable technology for production of complex-shaped, three-dimensional tumor model. Moreover, tumor induced animal is expensive, require extensive animal killing and is time consuming. For this reliable and efficient 3D in vitro tumor model is essential, which can reduce the time gap from bench to bedside.

Functional Amyloid Hydrogel for Drug Delivery Applications

The present invention provides the functional amyloid hydrogels, which are thixotropic in nature; therefore, they can also be employed as an implantable drug-delivering depot. Moreover, in the scenario where the existing technologies and techniques exhibit limitations regarding biodegradability, biocompatibility, and immunogenicity, the present invention is advantageous as the given hydrogel drug delivery system has the necessary properties to act as a long-acting depot. Since, there is no chemical cross-linking involved between the drug and carrier, the activity of the encapsulated drug is maintained. The added advantage is that the amyloid fibril formulation protects the biological, physical and chemical integrity of the drug molecules within the very stable cross-β-sheet structure during processing, storage and even upon delivery. Furthermore, an amyloid-binding component from the host organism reduces the potential immune response against the formulation. In addition, such a formulation can be easily administered by subcutaneous injection. The hydrogel protects the payload and increases the half-life of the encapsulated drugs; thereby minimizing repetitive dosage treatment. Also, there is no complicated manufacturing method involved with the synthesis thus reducing the cost. Being a protein/peptide material, the end products of these hydrogels are amino acids that can be easily metabolized by biological systems. Hence as a drug delivery vehicle, these hydrogels will not pose any additional harm in terms of by-products of metabolism.

In one embodiment, the present invention provides a method for developing a delivery agent for a biologic, the method comprising of:
 a. dissolving the functional amyloid hydrogels as described herein to obtain a solution of the hydrogel;
 b. mixing a biologic with the solution of the hydrogel to obtain a mixture solution; and
 c. maintaining the mixture solution at room temperature for 10-30 mins to obtain the delivery agent for a biologic.

The biologic as used in the method described herein is selected from small molecules, a peptide, a protein, a drug, and a therapeutic agent.

The method for developing a delivery agent for biologics includes the following steps:
 (a) Designing and preparation of the functional amyloid hydrogels
 (b) Testing gelation of the hydrogels by the gel inversion test
 (c) Determining the biocompatibility of the hydrogels
 (d) Dissolving the functional amyloid hydrogels as described herein to obtain a solution of the hydrogel;
 (e) Mixing a biologic with the solution of the hydrogel to obtain a mixture solution;

(f) Maintaining the mixture solution at room temperature for 10-30 mins to obtain the delivery agent for a biologic.
(g) Loading biologics comprising small molecules, peptides such as doxorubicin, retinoic acid and various proteins into the hydrogels
(h) Monitoring the release kinetics of the encapsulated biologic from the hydrogels
(i) Functionality assay of the released biologic both in vitro and in vivo.

In the method for developing a delivery agent, the selected biologics can be any protein, drug, therapeutic agent such as bovine serum albumin, doxorubicin, retinoic acid, but not limited to it.

The biologic is mixed with a hydrogel solution in the ratio of 1:10 of biologic and hydrogel.

The mixture of the hydrogel solution and the biologic is maintained at room temperature for gel formation. Upon gel formation, the biologic is entrapped within the gel to form the drug delivery agent.

For drug delivery studies, anticancer agent doxorubicin (DOX) and neuronal differentiating agent trans-retinoic acid (RA) were immobilized inside the amyloid hydrogels. The drug/protein gets encapsulated inside the amyloid hydrogel without any chemical cross-linking. The FITR studies revealed that encapsulation of payload does not alter the secondary structure of the hydrogel significantly. Moreover, the in vitro release assay was performed by encapsulating various small molecules and tagged proteins in newly developed functional amyloid hydrogels. The release profile of the encapsulated drug/protein/peptide showed that there is an initial burst release for the payload, which is followed by sustained and controlled release for extended time period. Further, the drug delivery capabilities of these designed hydrogels were directly tested by treating DOX encapsulated hydrogels and RA encapsulated hydrogels on MDA-MB-231 and SH-SY5Y cells respectively. Both small molecules were released in a controlled and sustained manner from the hydrogels. The released DOX resulted in—almost 70% cancer cell death and the released RA induced differentiation of SH-SY5Y cells towards neuronal lineage. These studies provide proof of concept/suggest the ability of these functional amyloid hydrogels as effective drug delivery agents. For another study, insulin was encapsulated in the hydrogels and subcutaneously injected into STZ-induced diabetic rat model. The blood sugar level and the serum insulin levels imply that the blood sugar level dropped to the normal range of about 100-120 (mg/dL) and was maintained for a few days.

Functional Amyloid Hydrogel for Wound Healing:

The present invention describes gels, which provide a nanofibrillar matrix to which cells attach and migrate into the wound site. The hydrogel scaffolds disclosed herein is a meshwork of nanofibers, which allow cell infiltration and cell to cell interaction. In one of the embodiments it may resemble the in vivo milieu and on directly injecting it may facilitate wound healing and regeneration by migration of cells to the center of the wound site. For example, they may be injected into chronic wounds, skin lesions, biopsy sites, ulcers or non-surgical wound sites. The free flowing feature of the hydrogel upon mechanical shear enables it to completely fill and fit the wound site, covering all the crevices at the edges of the injury.

In one embodiment, the present invention provides a method for developing a wound healer comprising functional amyloid hydrogel as described herein, wherein the functional amyloid hydrogel comprises biological agents.

In one embodiment, the biological agents include growth factors. The wound healer is adapted for treating wound introduced in confluent cells such as fibroblasts.

The present invention also relates to a method for developing wound healer, the method comprising:
(a) Designing and preparation of the functional amyloid hydrogels
(b) Testing gelation of the hydrogels by the gel inversion test
(c) Determining the biocompatibility of the hydrogels
(d) Dissolving the functional amyloid hydrogels as described herein to obtain a solution of the hydrogel;
(e) Mixing a growth factors with the solution of the hydrogel to obtain a mixture solution;
(f) Culturing of L929 fibroblast cell line till confluency.
(g) Creating a scratch with 200 µl tip followed by capturing of images to estimate the scratch area.
(h) Covering the wound area with functional amyloid hydrogel with/without growth factors and PBS as a control.
(i) Estimation of wound closure with days compared to control.

Other features and advantages of the present invention are apparent from the following detailed description and examples which should not be construed as limiting. The contents of all references, patents and published patent applications cited throughout this application are expressly incorporated herein by reference.

ADVANTAGES OF THE PRESENT INVENTION

Our invention describes hydrogel designed from functional amyloid sequences, mainly protein/peptide hormones but this can be extended to any functional as well as non-toxic amyloids, where the most aggregation-prone regions was selected for nanofabrication of hydrogels. Peptides self-assemble spontaneously by adjusting the pH, temperature and salt and/or ion composition of the peptide solution. Further, these hydrogels are thixotropic in nature; they can be easily converted from gel to sol state and vice versa. This property makes them readily suitable for loading various small molecules, polymer and cells. In addition, the mechanical strength and the chemical composition of the hydrogel can be controlled through manipulation of the amino acid sequence and gelation parameters. Since functional amyloids sequences are biologically useful, they would be less cytotoxic and their cross-seeding, amplification and transmissibility characteristics might be highly reduced, unlike disease-associated amyloids. All these factors ensure functional amyloid hydrogel as a potential candidate for various biotechnological applications including drug delivery, tissue engineering, tissue adhesive, and organoid/tumoroid development for cancer drug testing and personalized medicine. For example, this class of biomaterial has several advantages as a scaffold for cell adhesion, differentiation, developing 3D tumor models and drug delivery purposes. First, nanofiber network of the amyloid hydrogel resembles ECM and provides a truly 3-D environment for cells to grow, migrate, proliferate and differentiate. Second, biomolecules in such a nano-scale environment diffuse slowly and are likely to establish a local molecular gradient more closely mimicking the in vivo scenario. Third, the degradation products of such peptide scaffolds are naturally occurring amino acids, potentially reducing their cytotoxicity and immunogenicity. Moreover, in context with existing methodologies in case of 3D tumor model, no other biophysical or biochemical cues are required for formation of the spheroid using the present scaffold. Products designed on this scaffold can support applications ranging from small scale exploratory studies to fully automated drug screening campaigns and even for clinical use. Immediate testing of drugs in these organoids/tumoroid may ultimately aid in choosing the best therapy for the patient, manifesting the personalized approach to treating cancer. These tumoroid/spheroids accurately represent the primary tumor and show potential for quick development and low-cost, comprehensive testing of novel therapies moving 3D drug discovery into the age of precision medicine. Also, in terms of amino acid length, shorter peptides offer the advantage of lower cost, greater ease of synthesis, and higher solubility and purity. Furthermore, shorter peptides show less structural and chemical complexity, which facilitates their study and potential uses. Overall, the present invention will provide a scaffold for cell adhesion and tissue engineering, a cheap and easy to generate spheroids technology of any desired cancer lines for evaluating anticancer drug and thus, eliminating the major concern of the 3D technology till date and aid as a depot for controlled and sustained release of biologics.

Henceforth, embodiments of the present disclosure are explained with one or more examples. However, such examples are provided for the illustration purpose for better understanding of the present disclosure and should not be construed as limitation on scope of the present disclosure.

EXAMPLES

Example 1: Designing Functional Amyloid Hydrogel

Figure 1:
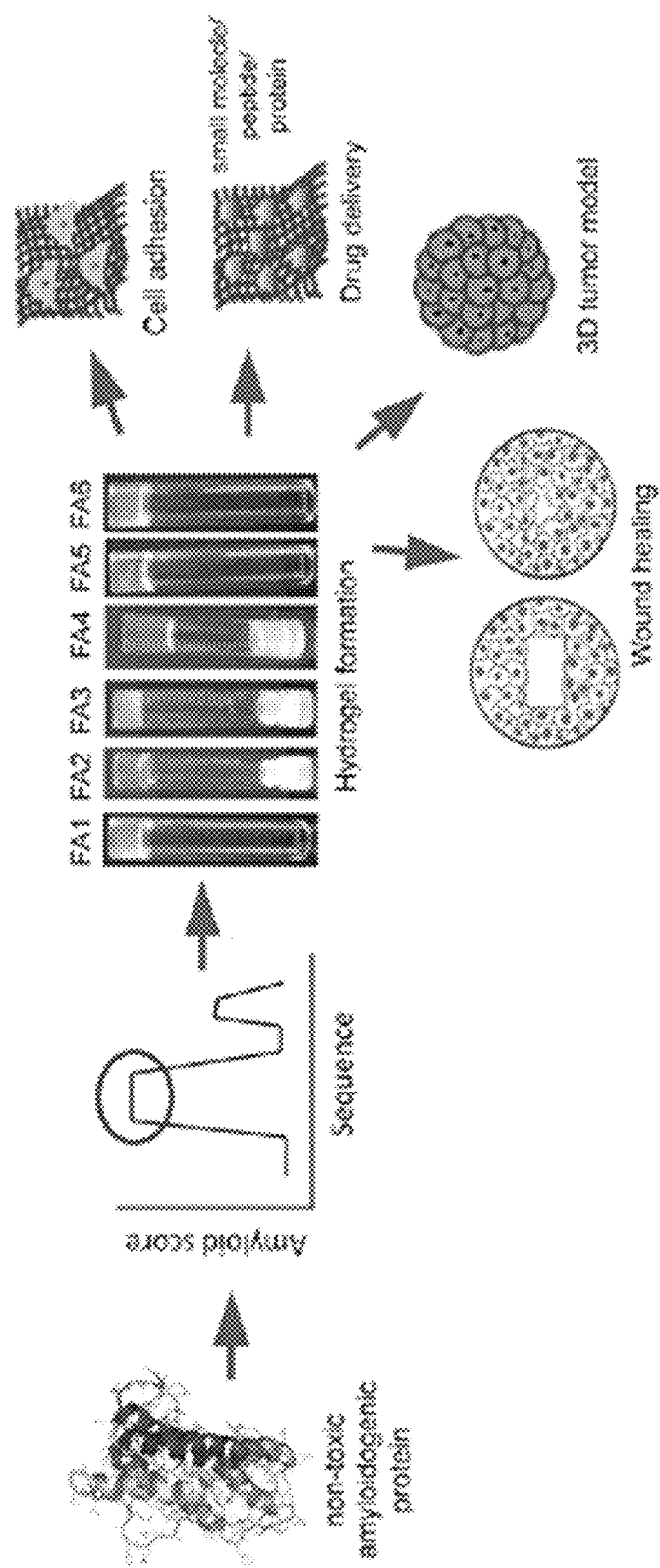

The hydrogel forming peptides were designed based on the self-assembly of high amyloidogenic segments from various functional amyloid protein/peptides. FIG. 1 depicts the scheme for designing the peptide sequence of the functional amyloid hydrogel. For example, the most amyloidogenic segment from non-toxic amyloid protein was selected by the amyloid segment-predicting algorithm TANGO. The rapid intermolecular hydrogen bond formation of these amyloidogenic peptide sequences would give rise to amyloid fibril networks, which would subsequently form functional amyloid hydrogel by entrapping the water. Moreover, the basic sequence was further modified with addition and substitution of other amino acids to create more peptides along with Fmoc protection at the N-terminus.

Example 2: Preparation of the Functional Amyloid Hydrogel

In brief, 1 mg of each pre-synthesized peptide was dissolved in 200 μl of 20 mM phosphate buffer at pH 7.4 by heating. Subsequently, three heating/cooling cycles and the addition of 150 mM NaCl were performed that resulted in self-sustaining hydrogels. For pH dependent hydrogels, 200 μl of 20 mM phosphate buffer at pH 7.4 was added to peptide, to dissolve the peptide, the pH was initially increased to 10 using 2N NaOH to dissolve the peptides and then decreased to 7.4 for gelation. Few peptides did not require salt for gelation.

Hydrogel preparation: Generally, 1 mg of lyophilized powder of each designed peptide was suspended in 200 μl of 20 mM sodium phosphate buffer (pH 7.4) and the pH was increased till the peptides dissolve in the buffer. On dissolution the pH of the gel solution was brought back to physiological pH 7.4 and 0-300 mM NaCl was added.

Gelation study: The gel solution was kept undisturbed at room temperature for 15 mins and gelation was determined by the gel inversion test. The hydrogel stayed at the bottom of the tube on inversion, indicating stable hydrogel formation, which is shown in FIG. 1.

Figure 2A:
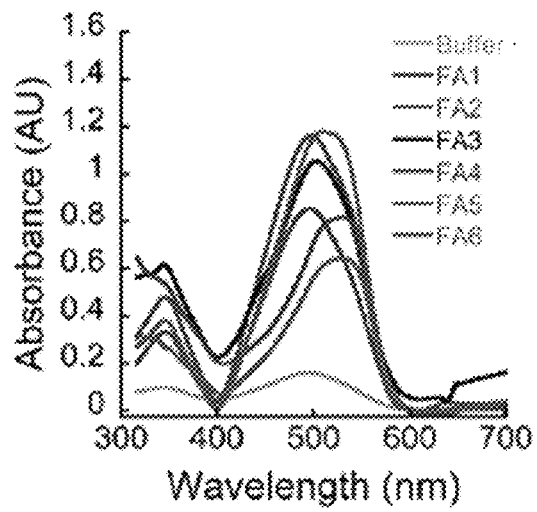
Figure 2B:
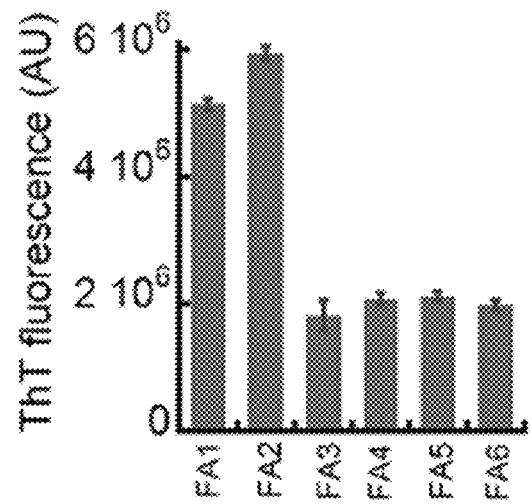
Figure 2C:
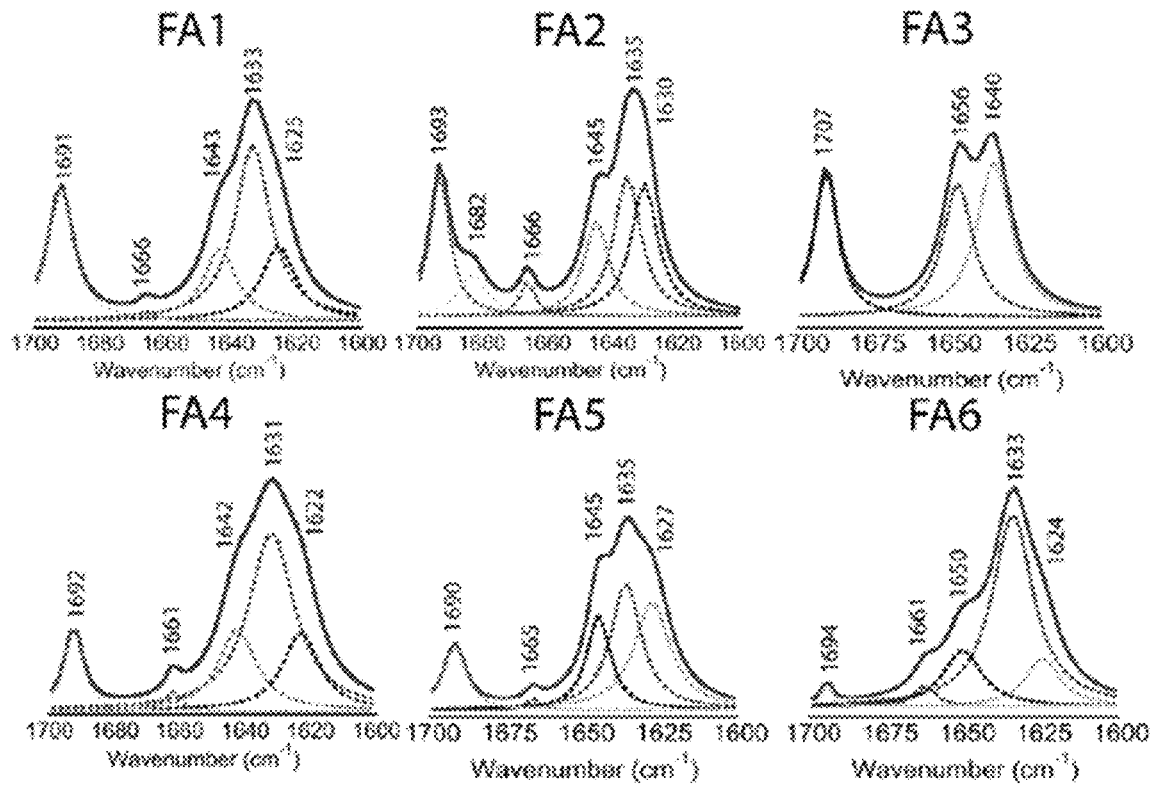

To demonstrate the presence of amyloid nanofibrils, the hydrogels was determined with Congo red stain or Thioflavin T dye binding. FIG. 2A depicts the Congo red binding ability of the designed hydrogel. The peptide gels showed an increase in CR absorption and red shift of $\lambda_{max}$ suggesting that self-assembly and gelation are results of higher order assembly of amyloid fibrils. FIG. 2B shows the ThT binding assay revealing high binding of ThT dye to amyloid fibrils of the hydrogels, indicating their amyloidogenic nature. To determine the secondary structure of the hydrogel, Fourier transform infrared spectroscopy (FTIR) studies were also performed. FIG. 2C depicts the FTIR spectra of the peptide components of the hydrogels. The FTIR spectra (1500-1800 cm$^{-1}$) was recorded and the raw data was deconvoluted and curve fitted FTIR spectra in the range of 1600 cm$^{-1}$ to 1700 cm$^{-1}$ (amide-I band). The hydrogels showed peaks in the range of ~1630 and ~1690 cm$^{-1}$ indicating β-sheet formation upon gelation.

Figure 3:
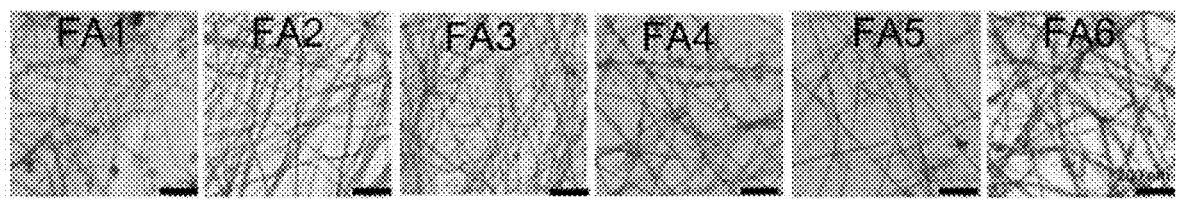
FIG. 3 depicts the morphology of the functional amyloid hydrogel as observed by the TEM image.
Figure 4:
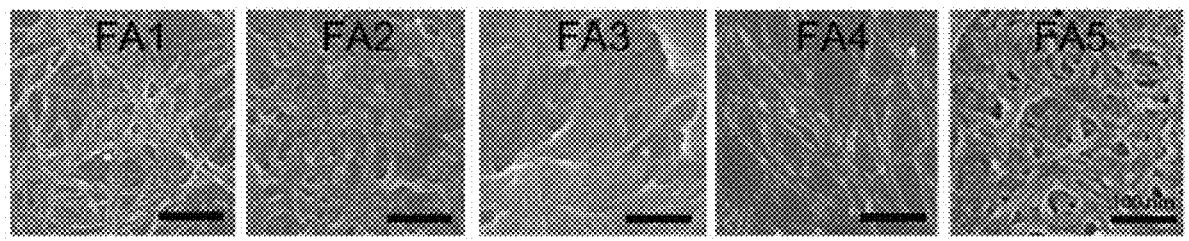
FIG. 4 shows a SEM image, which depicts the nano-fibrillar nature of the hydrogel.
Figure 5:
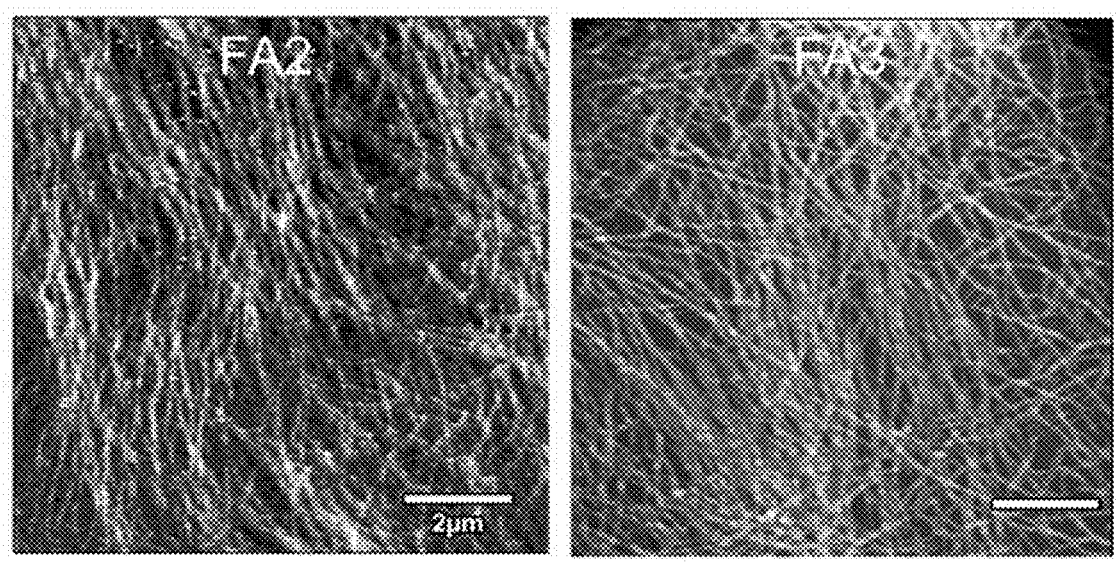
FIG. 5 shows the AFM image, which confirms the fibrillar morphology of the functional amyloid hydrogel
Figure 6:
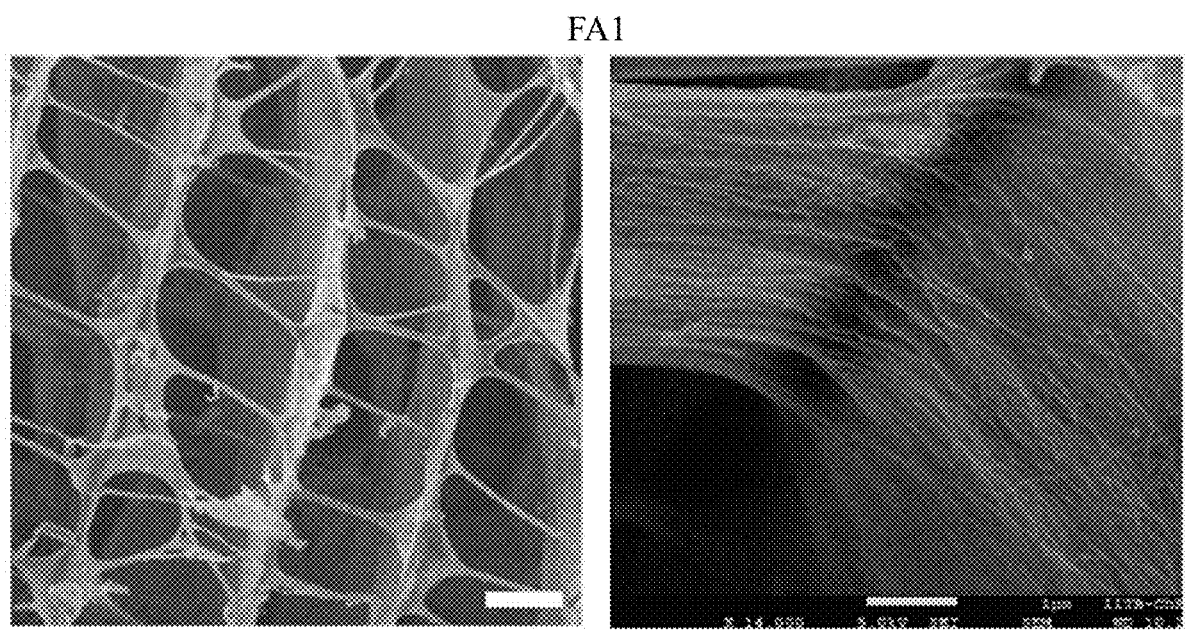
FIG. 6 depicts the pore size of the hydrogel as seen by the cryo-SEM image.

Electron Microscopy: Transmission electron microscopy and scanning electron microscopy was used to visualize the nano-fibrillar nature of the hydrogel. FIG. 3 depicts the morphology of the hydrogel as observed by the TEM image. The study revealed that the hydrogels are composed of nano-fibril network and the fibrils possess morphology similar to amyloid fibrils. FIG. 4 shows SEM image, which depict the nano-fibrillar nature of the hydrogel. The AFM study also confirmed the fibrillar morphology of the functional amyloid hydrogel (FIG. 5). The pore size of the hydrogels was shown by cryo-SEM study as shown in FIG. 6.

Example 3: Measurement of Hydrogel Swelling

Figure 7:
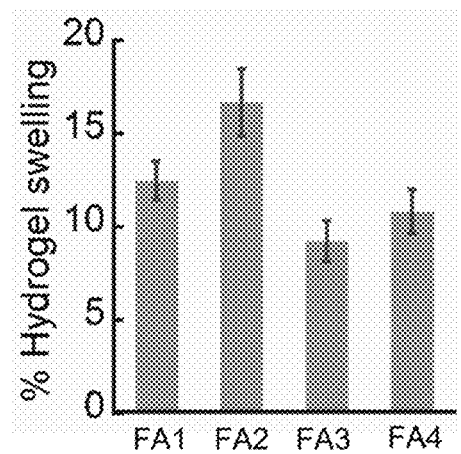
FIG. 7 depicts the swelling measurement of the amyloid hydrogels.

To determine the dynamic swelling measurements of hydrogels, gravimetric method was used. The hydrogel samples were casted on cover slips and inserted in a well of 24 well plates containing PBS and incubated at 25° C. At different time points the hydrogel sample was taken out from the well, quickly blotted of free surface buffer, weighed in an analytical balance and quickly returned to the well with PBS. FIG. 7 depicts the swelling measurement of the hydrogels, which shows that the gel swells on addition of any kind of solvent/media/buffer.

Example 4: Rheological Studies of the Hydrogel

To determine the rheological properties of the amyloid hydrogel, rheology measurements were performed to determine the storage modulus and loss modulus of the hydrogels. Small strain amplitude oscillatory rheology measurements were performed on an Anton Paar rheometer (Graz, Austria) with a parallel plate (diameter of 25 mm; PP25). The measurements were taken at 37° C. in dynamic oscillatory mode with constant amplitude of 0.05% and a gap size of 0.2 mm. The frequency sweep was performed with an angular frequency (ω) of 100-0.1 s-1 for 15 min. The linear visco-elastic region was determined from a preliminary strain sweep from 0.01% to 100% at a constant frequency.

For determining the thixotropicity of the hydrogel, the step-strain oscillatory rheology was performed. A high strain (100%) was applied to the hydrogel followed by low strain (0.5%). The storage modulus (G') and loss modulus (G") of the hydrogels is shown in FIG. 8. FIG. 8A depicts the Oscillatory rheology studies of amyloid hydrogel for presenting the storage modulus (G') and loss modulus (G"). In FIG. 8A, FA1, FA2, and FA4 gels showed the storage modulus higher than the loss modulus, a property typically seen for visco-elastic materials. The storage modulus of FA1 hydrogel exhibited the highest storage modulus of ~1000 Pa, FA2 gel showed a maximum storage modulus ~1070 Pa and FA4 showed a storage modulus of ~550 Pa at 100 Hz frequency. FIG. 8B depicts the thixotropic nature of the hydrogel by stress-strain rheological measurement of the hydrogels. The results of this experiment showed that gels FA1, FA2, and FA4 were found to readily transform into solution state after applying high shear stress ($\gamma=100\%$; $\nu=1$ Hz), yielding a drop in the storage modulus (G') to a value below the loss modulus (G"). However, when the strain amplitude was decreased ($\gamma=0.05\%$) at the same frequency, the G' value was instantly increased to its initial value and transformed into a semi-solid (gel) state (FIG. 8B).

Example 5: Assessment of Cytotoxicity of the Functional Amyloid Hydrogel

To determine whether the functional amyloid hydrogel is non-toxic in nature, MTT (3-[4,5-dimethylthiazol-2-yl]-2,5 diphenyl tetrazolium bromide) assay was performed. The amyloid hydrogels were casted at a concentration of 5 mg/ml for each peptide and neuroblastoma, SH-SY5Y cells at a density of $10^4$ were seeded and cultured on the hydrogels for 24 hours. The MTT reagent (0.5 mg/ml final concentration) was added to the cells after 24 hrs of culture and the cells were further incubated for 4 h. Finally, 100 μl of 50% N, N-dimethylformamide/20% sodium dodecyl sulfate solution was added, and the mixture was incubated overnight. The absorption was then measured at 560 nm with an automatic microtiter plate reader (Thermo Fisher Scientific, Waltham, MA, USA). FIG. 9 depicts the percentage of cell viability. The MTT assay showed that cells grown on scaffolds FA1, FA2, FA3, and FA4 showed more than 80% cell viability, suggesting that these peptide hydrogels are compatible for cell culture.

Example 6: Culture of Cell Lines

Cell lines (MCF-7, HepG2, HeLa, A549, SH-SY5Y and MDA-MB-231) were cultured in tissue culture flasks under standard conditions (37° C., 5% $CO_2$, 95% humidity) in DMEM media supplemented with 10% heat inactivated fetal bovine serum. Bone-marrow derived hMSCs was cultured in knockout DMEM media supplemented with 10% FBS, 1× Glutamax and 0.25× antibiotic cocktail under similar conditions. All mammalian cell lines used in the study were obtained from the cell repository at the National Centre for Cell Science, Pune, India.

Example 7: Preparation of 2D Culture of SH-SY5Y and hMSCs Using Functional Amyloid Hydrogel SH-SY5Y and hMSCs cell were grown in their respective culturing conditions. For 2D culture, the hydrogel was casted on 12 mm treated coverslips and both SH-SY5Y and hMSCs were cultured on them. The area of cell spread was determined (FIGS. 10A, 10B and 10D).

Example 8: Preparation of 3D Culture of hMSC Using Functional Amyloid Hydrogel

For culturing cells in 3D, $1\times10^4$ hMSCs were trypsinized and was mixed immediately with 50 μL of vortexed hydrogels. The cell and hydrogel mixture were then casted on a coverslip and allowed to solidify before adding culture media. The setup was then kept undisturbed for 30 min. Owing to the thixotropic property the hydrogels, within 20 min, the gel form was regained with encapsulating the cell. The culture media was added post hydrogel gelation (FIG. 10C).

Example 9: Immunostaining for β-III Tubulin and Actin Expression in 2D Cell Culture of SH-SY5Y and hMSC The cells were fixed in 4% paraformaldehyde for 15 mins in case of 2D and 1 hr for 3D in the dark at room temperature. After fixation, the cells were permeabilized (0.5% TritonX-100 for 20 minutes), followed by blocking with 1% BSA for 30 minutes. The cells were then treated with rabbit monoclonal primary antibody against β-III tubulin (1:500 dilutions) and actin (1:500 dilutions) at 4° C. for 16 hours. For SH-SY5Y, Alexa Fluor 555 conjugated anti-rabbit secondary antibody was used in 1:1000 dilution and Alexa 488 conjugated anti-rabbit secondary antibody (1:500) in case of hMSCs, for 2 hours followed by washing with PBS and DAPI (1 μg/ml) staining for 5 mins. Finally, after PBS washing, the cells were mounted and visualized under Leica Dmi8 fitted with a sCMOS camera (Andor Technologies) (FIG. 10B and FIG. 23B).

Example 10. Gene Expression Analysis of Neuronal Markers in 2D-Cell Culture

The RNA isolation was performed by Trizol Method and cDNA was synthesized according to the manufacturer's protocol. To investigate the expression profile of GRIA3, TUBB3 and ENO gene, which are the neuronal markers. RNA was isolated from 2D culture of hMSCs. This was followed by respective cDNA synthesis. The gene expression was analyzed by Real-time PCR technique. GRIA3, TUBB3 and ENO gene were found to be upregulated in all the cases, while GFAP gene was down-regulated (FIG. 10E).

Example 11: Method of Spheroid Formation

Cells were trypsinized using 1× trypsin-EDTA, and 10000 cells were pelleted and mixed with 20 μl of hydrogel and seeded in three or four drops on the cover slip and incubated for a few minutes for hydrogel to solidify a little. The ratio of cells to hydrogel was determined empirically such that cells are in close proximity to each other. Fresh medium (DMEM media supplemented with 10% heat inactivated fetal bovine serum) was added in the wells slowly without disturbing and kept for 10 days for spheroid formation. Viability of cells was analyzed through Trypan Blue cell exclusion assay. FIG. 11 describes morphological changes and growth kinetics by all different cell lines with days cultured on FA1 hydrogel for 9 days. Images indicated that after 24 hours, cells start migrating towards each other and finally into mature spheroids in five days. Formation of spheroid followed the procedure as reported in the previous literature and indicated that the all gels supported 3D spheroid formation irrespective of cell lines and their origin. In the Day 1, cells were started clustering towards themselves followed by Day 3 indicative of increase of cadherin expression. Multiple cells started to form clusters due to the seemingly random cell migration and cell-cell adhesion. These premature spheroids kept growing larger and denser, and finally became mature with significant thickness and clear 3D structure at day 5. The diameter range of spheroids was from 50-500 µm. Hydrogel provided physical and structural support for the formation of a 'natural' setting that better recapitulates cell behavior in vivo.

Example 12: Measurement of the Growth Kinetics of the Spheroids

Figure 12A:
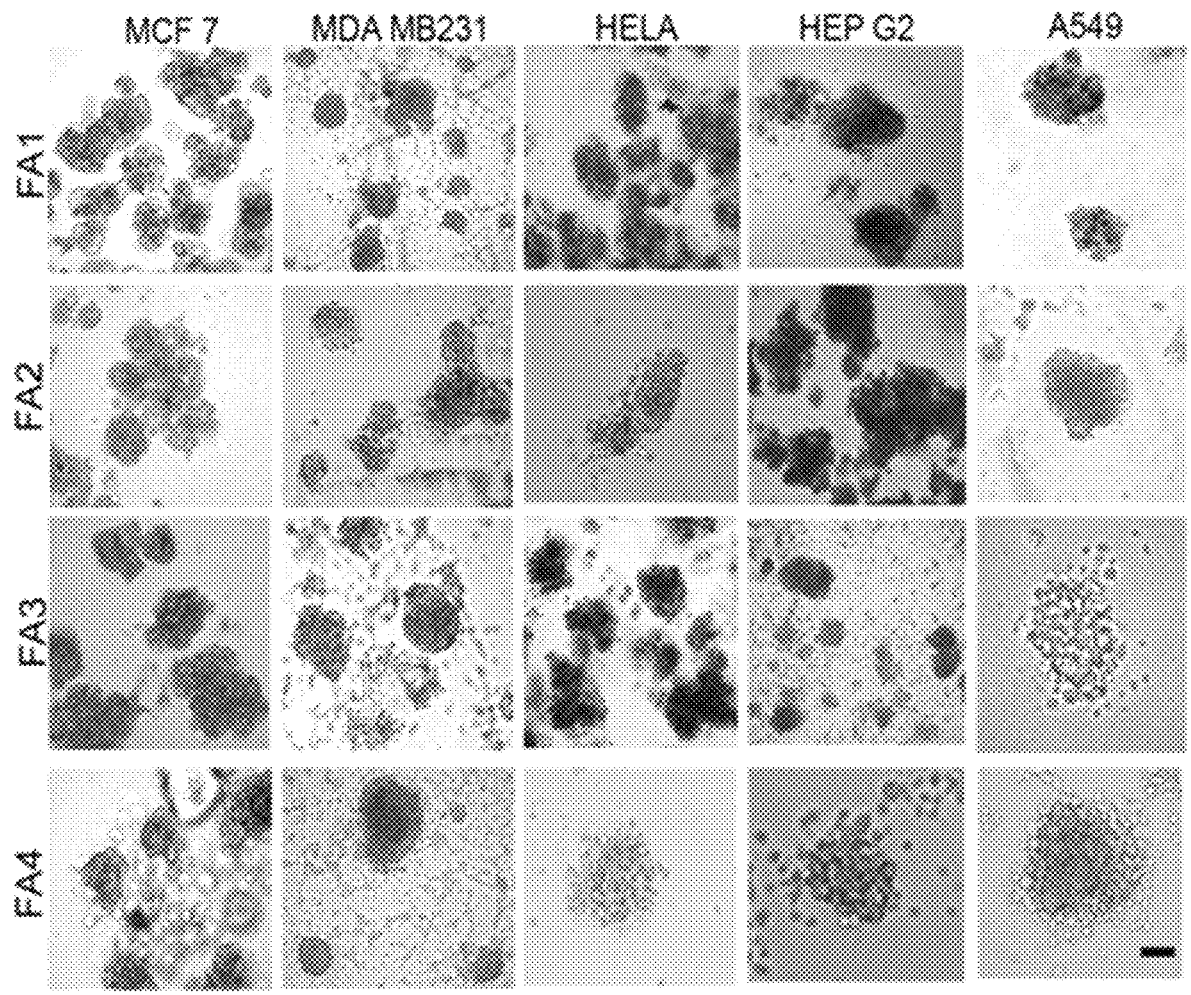
Figure 12B:
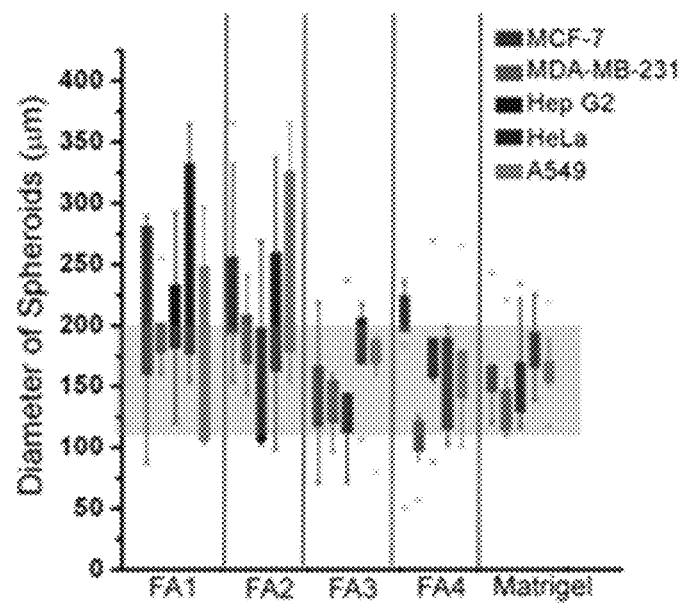
Figure 12C:
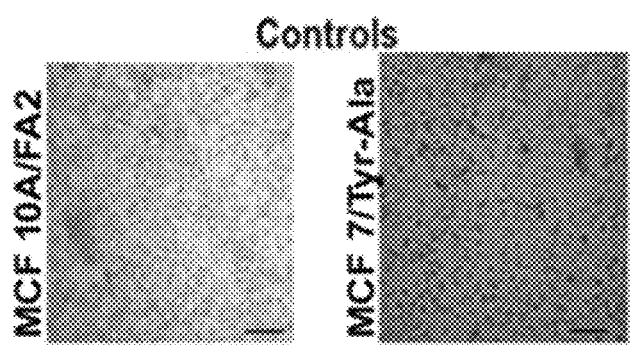

Formation of spheroid was monitored every alternate day by capturing images using Leica Dmi8 at 10× magnifications fitted with a sCMOS camera (Andor Technologies). Mean spheroid area was quantified every alternate day for all spheroids using ImageJ software assess the size of 3D cellular structures. FIG. 12A represents formation of spheroid with different cell lines cultured on different class of hydrogels and spheroid diameter after 5 days of culture and matrigel served as standard which was heterogeneous and between range 50-500 µM in size (FIG. 12B). MCF 10 A and Tyr-Ala gels were used as negative controls for cell and gel respectively and indicated no spheroid formation (FIG. 12C).

Example 13: Calcein AM-Ethidium Homodimer-1 Staining of Spheroids

Following incubation for 7 days in the medium, spheroids were stained with a mixture of two dyes: 1 µM calcein AM, 1 µM of ethidium homodimer-1. Dyes were prepared freshly in sterile phosphate-buffered saline and added directly to media without aspiration. Since dye penetration is slower into spheroids than 2D cultures, spheroids were incubated with dye for 2 h before imaging. Dye solution was washed out with PBS slowly, and care was taken during pipetting to avoid spheroid loss, disintegration, or displacement. FIG. 13 showed the viability assay of spheroids of different sizes on different day, using a live/dead staining with ethidium homodimer-1 and calcein-AM. Image indicated cell viability of MCF 7 spheroids and confirmed that this new state of the art hydrogel is biocompatible and non-toxic. Viable cells appear as green, while nonviable cells appear as red. The 8 day-old spheroid had visibly three regions, where densely packed cells at the centre of the spheroid representing necrotic core, mid region representing quiescent viable zone and outer most region is proliferating zone where, cells growing at the periphery.

Example 14: Immunostaining for Cadherin Expression in 3D vs. 2D Cell Culture System Spheroids after 7 days of incubation were fixed in 4% paraformaldehyde for 1 h in the dark at room temperature. After fixation, the cells were permeabilized using 0.5% Triton X-100 for 20 minutes, blocked with 1% BSA for 30 minutes. The cells were then treated with mouse monoclonal primary antibody against E-cadherin and rabbit monoclonal primary antibody N-cadherin (Sigma, USA) (1:1500 dilutions) at 4° C. for 16 hours. Alexa Fluor 555 conjugated anti-mouse and anti-rabbit secondary antibody (Life Technologies, USA) was used in 1:2000 dilution for 2 hours followed by washing with PBS and DAPI (1 µg/ml). Spheroids were visualized under Laser scanning microscopy.

In general, cadherins act as versatile cell-cell adhesion receptors and function as dynamic membrane-spanning macromolecular complexes. Previous studies indicated that cancers at an advanced stage often have abnormal E-cadherin expression. Hence elucidation of expression of cadherin in spheroid biology is important. FIG. 14 describes the presence of cadherin in spheroid during formation. Results indicated up regulation of cadherins in 3D as compared to 2D. Previous studies suggested that initial aggregation is due to upregulated cadherin expression. Red fluorescence indicated those spheroids are bound due to high expression level of cadherin. Images suggested rapid spheroid formation and strong staining of E-cadherin on MCF7 spheroids and N-Cadherin on HeLa spheroids on the surface of cells formed in the presence of free calcium as compared to 2D. Hence, images exhibit that cadherin accumulates on the membrane surface where, cells are compacted into solid aggregates to form spheroid due to the homophilic cadherin-cadherin binding. To validate the immunofluorescence data and importance of cadherin as an adhesive protein for spheroid formation, cell samples were supplemented with EGTA (ethylene glycol-bis(β-aminoethyl ether)-N,N,N',N'-tetraacetic acid), a calcium chelator in culture media to remove free calcium. Spheroids failed to form in medium supplemented with EGTA suggest an essential role of calcium-dependent adhesion protein such as cadherin. This experiment also substantiates the images observed in immunofluorescence indicating importance of cadherin in formation of the spheroids.

Example 15: Gene Expression Analysis of the Cancer Biomarkers

RNA Isolation was performed by Trizol Method and cDNA synthesis using manufacturer's protocol (NEB cDNA synthesis kit). To investigate the expression profile of potential cancer biomarkers in 3D compared to 2D culture was analysed. Firstly, RNA was isolated from MCF 7, MDA MB 231, Hep G2, A549, HeLa spheroids and their respective monolayer culture followed by cDNA synthesis. Gene expression was analyzed by quantitative Real time PCR. Markers analyzed have implication in cell cycle regulation, differentiation, and malignant transformation. Results indicated up-regulation of cancer biomarkers in 3D as compared to 2D (FIG. 15). Over-expression of this gene has been reported in numerous cancers, including breast and ovarian tumors. Hence, up-regulation of these angiogenesis markers as well as cell adhesion markers indicated that spheroids cultured on these hydrogels are able to mimic the tumor micro-environment.

Example 16: Drop-Cast Method of Spheroid Formation

Confluent cells were trypsinized using 1× trypsin-EDTA, and 10000 cells were pelleted and mixed with 10 µl of hydrogel and seeded in a form of drop on cover slip followed by incubation for 20 minutes for hydrogel to solidify a little. Fresh medium (DMEM media supplemented with 10% heat inactivated fetal bovine serum) was added in the wells slowly without disturbing and kept for 10 days for spheroid formation. FIG. 16 describes spheroid formation of different cell lines on functional amyloid hydrogels after 48 h.

Example 17: Microarray Analysis for Cancer Biomarkers

To identify genes that are differentially expressed between monolayers and spheroids, we performed a microarray analysis of MCF 7 spheroids cultured on FA1 and FA2 along with matrigel as a control grown in 2D and in 3D. RNA was extracted using RNA isolation kit followed by quality control test through bioanalyzer. Subsequently, human microarray analysis was performed in 8×60k array format followed by data analysis using Agilent gene spring software. FIG. 17 depicts up regulation and down regulation of cancer genes in 3D compared to 2D. Matrigel served as control.

Example 18. Effect of Anti-Cancer Drug on the Spheroids by MTT, Fluorescence Study and Live/Dead Staining of Cryospheroids Cytotoxicity assays by MIT: MCF7 spheroids were cultured for five days in DMEM (Dulbecco's modified Eagle's medium) with 10% FBS, in a 5% CO2 incubator at 37° C. followed by treatment with different chemotherapeutics drugs (0-14 µM) for 24 h. For control, media containing buffer. After 24 h of incubation, 10 µl of MTT solution (5 mg/ml prepared in PBS) was added to each well and incubated for 4 h. Subsequently, 100 µl of SDS-DMF solution (50% DMF and 20% SDS, pH 4.75) were added and kept for overnight incubation. The absorption values at 560 nm and 690 nm (background absorbance) were determined using a SpectraMax M2e microplate reader (Molecular Devices, USA). The cell viability was plotted as percentage cell viability by considering 100% viability for the buffer control (FIG. 18 A).

Dense spheroids tended to show relative resistance to all these five chemotherapeutic drugs in the 3D-culture as compared to this resistance in 2D. Hence $IC_{50}$ for all the drugs for 3D was much higher than 2D. Spheroid cultured on FA 1 and 2 showed highest resistances to these drugs. For 5FU, there was more death in 3D as compared to other drugs for above-mentioned concentration. These findings confirm that the formation of dense spheroids in 3D-culture plays a role in determining the sensitivity of the cell lines to these chemotherapeutic drugs. The entire phenomenon suggests that beyond simple diffusion limitations in 2D Vs. 3D, geometrical difference can have far-reaching impacts in terms of understanding physiological response.

Fluorescence study was also performed to observe the effect of drug on 2D versus 3D. Here, after maturation of spheroids i.e., 5 days of culture on gel 4, different dose of paclitaxel (2-10 µM) was added for 24 h. To assess the effect of drug, cell viability was observed by staining through calcein AM and ethidium homodimer-1. Images were captured after incubation with dyes for 1 h. Captured images exhibited that 3D are more resistant than 2D where, the compact structure of the 3D does not allow the drug to penetrate similar to 2D. On the other hand, at the concentration of 4 µM, 70% of the cells for 2D are dead for the drug paclitaxel (FIG. 18 B).

Cryopreservation of spheroids: The spheroid after 2nd day of incubation was transferred into cryovials (1 well/vial). The medium was replaced with 1 ml of cryoprotective solution containing 10% dimethyl sulphoxide (DMSO) and 30% FCS in breast organoid medium at 4° C. Freezing of spheroids were done by stage-wise cooling procedure. Initially, the vials were kept at 4° C. for 1 hour followed by at −20° C. for 3 hours. Finally, the vials were placed into liquid nitrogen (−196° C.). Before preservation, spheroids were stained for viability with calcein-AM and ethidium homodimer-1 (FIG. 18C). For recovery, spheroids were thawed in a water bath (37° C.) for 2-3 minutes after removal from the liquid nitrogen. After thawing, the cryoprotectant was replaced with fresh suitable culture medium followed by washing twice with fresh culture medium. Subsequently transferred to 24-well plates and then stained with calcein-AM and ethidium homodimer 1 staining for determining cell viability (FIG. 18 C).

Example 19: Breast Tumor (BT) Tissue Processing

BT tissues were snapped after arrival and chopped into 1-3 mm³ pieces. Four random pieces were snap frozen and stored at −80° C. for DNA isolation, four random pieces were fixed in formalin for histopathological analysis and immunohistochemistry, and the rest was processed for the isolation of viable cancer cells. The tissue was minced, washed with (Advanced DMEM/F12 containing 1× Glutamax, 10 mM HEPES, and antibiotics) and digested in 10 mL BC organoid medium containing 1-2 mg·ml$^{-1}$ collagenase on an orbital shaker at 37° C. for 1 h. The suspension was given short spin to remove big chunks of tissue pieces. Subsequently, 2% FCS were added to the suspension before centrifugation at 1200 rpm. The pellet was resuspended in 10 ml BC organoid medium. Cells were counted using haemocytometer. Viability of cells was observed by trypan blue.

Figure 19A:
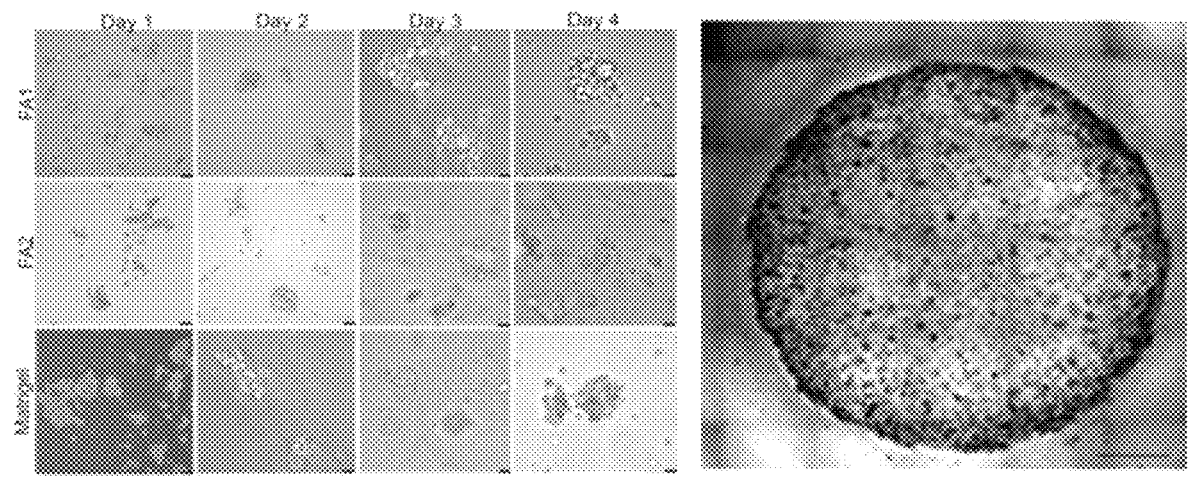

Example 20: Formation of Breast Cancer Tumoroids by Spread and Drop Cast Method, Viability and Drug Testing Breast cancer tumor cells were plated on functional amyloid hydrogels (For example FA 1) along with matrigel as a positive control and were initiated for organoid formation through spread and drop cast method in suitable media and monitored for days (FIG. 19A).

Breast Cancer Organoid Culture Through Spread and Drop Cast Method:

Spread method. 10 µl of hydrogel was spread on 10 mm cover slip as bed for forming spheroids. Subsequently, mixed with 10000 cells and spread over the slip and incubated at 37° C., 5% CO2, 95% humidity in BC organoid media for days. Spheroid formation was checked every alternate day. Viability of cells was analyzed through Trypan Blue cell exclusion assay.

Figure 19B:
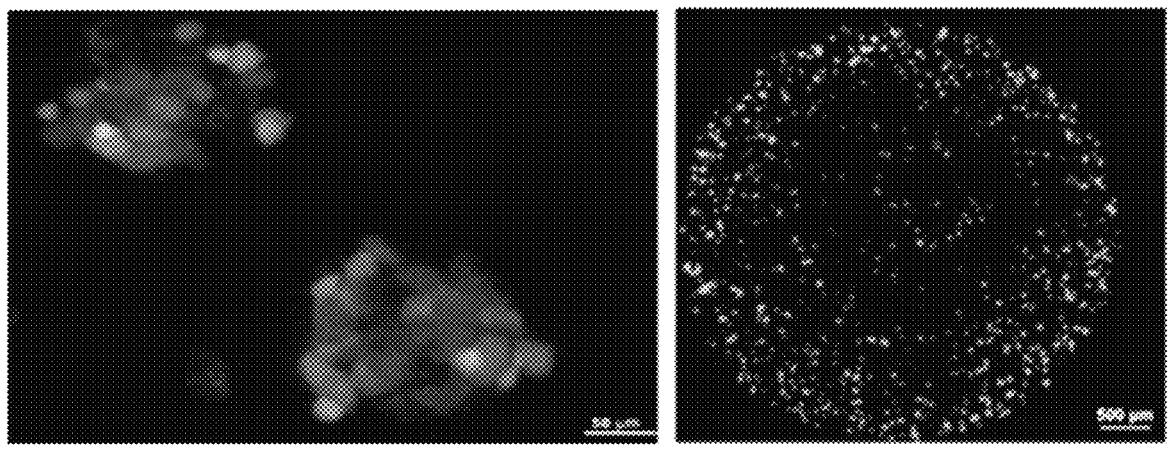

Drop cast method. 10 µl of hydrogel was spread on 10 mm cover slip as a bed for forming spheroids. Subsequently, 10 µl of hydrogel was mixed with 10,000 cells and drop cast in the form of drop on cover slip and were allowed to solidify on at 37° C. for 20 min. Upon completed gelation, 400 µL of BC organoid medium was added to each well and plates transferred to humidified 37° C./5% $CO_2$ incubators. Medium was changed every 4 days and organoids were passaged every 1-4 weeks were analyzed for the growth kinetics. Viability of cells was analyzed through Trypan Blue cell exclusion assay and while, viability of spheroids were analyzed using calcein-AM and ethidium homodimer-1 staining (FIG. 19B).

Figure 19C:
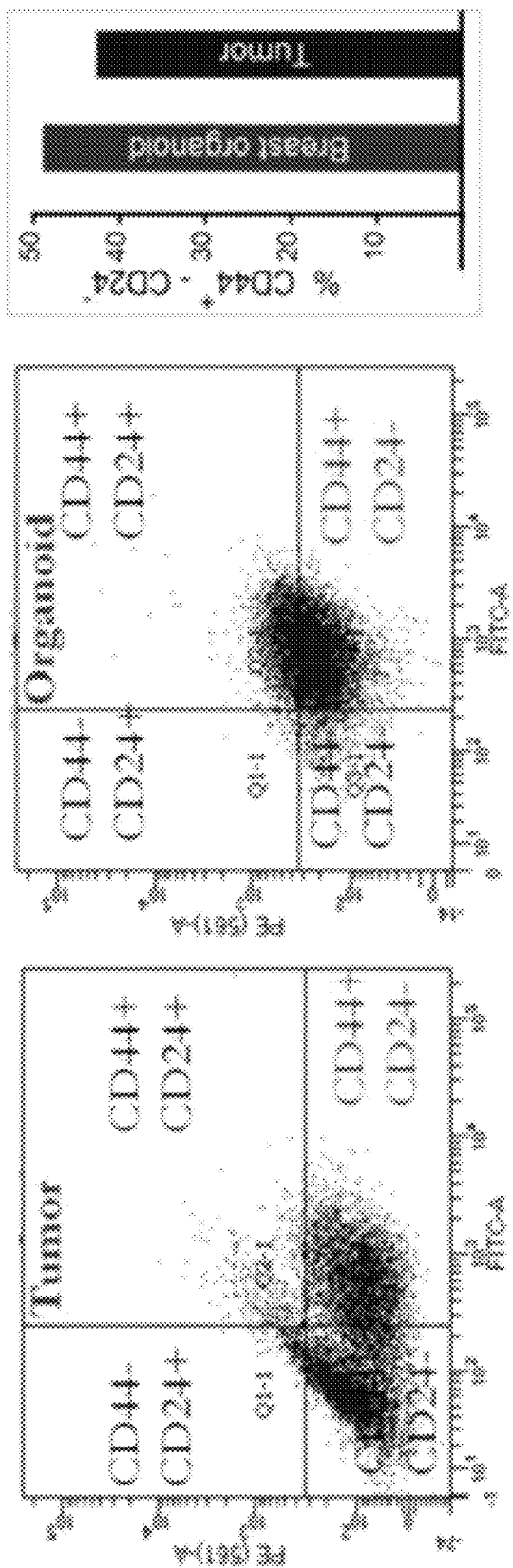

Images indicated that these gels were reliable scaffold for generation of organoid. Cells of different shape and size which are indicative of heterogeneous population came closer initially to form small aggregates and eventually developed into bigger aggregates and eventually tested cell viability and drug efficacy (FIG. 19). FACS analysis for drug testing on breast cancer organoids:

Example 21: Estimation of CD44+/CD24− Populations in Breast Tumor and Generated Organoid Breast tumor cells and generated tumoroids were sorted by flow cytometry for CD44+/CD24− population using CD44+-FITC tagged antibody and CD24− PE tagged antibody. Further the population of distributed CD44+/CD24− in percentage was plotted by number of sorted cells in the respective quadrant (FIG. 19C).

Figure 19D:
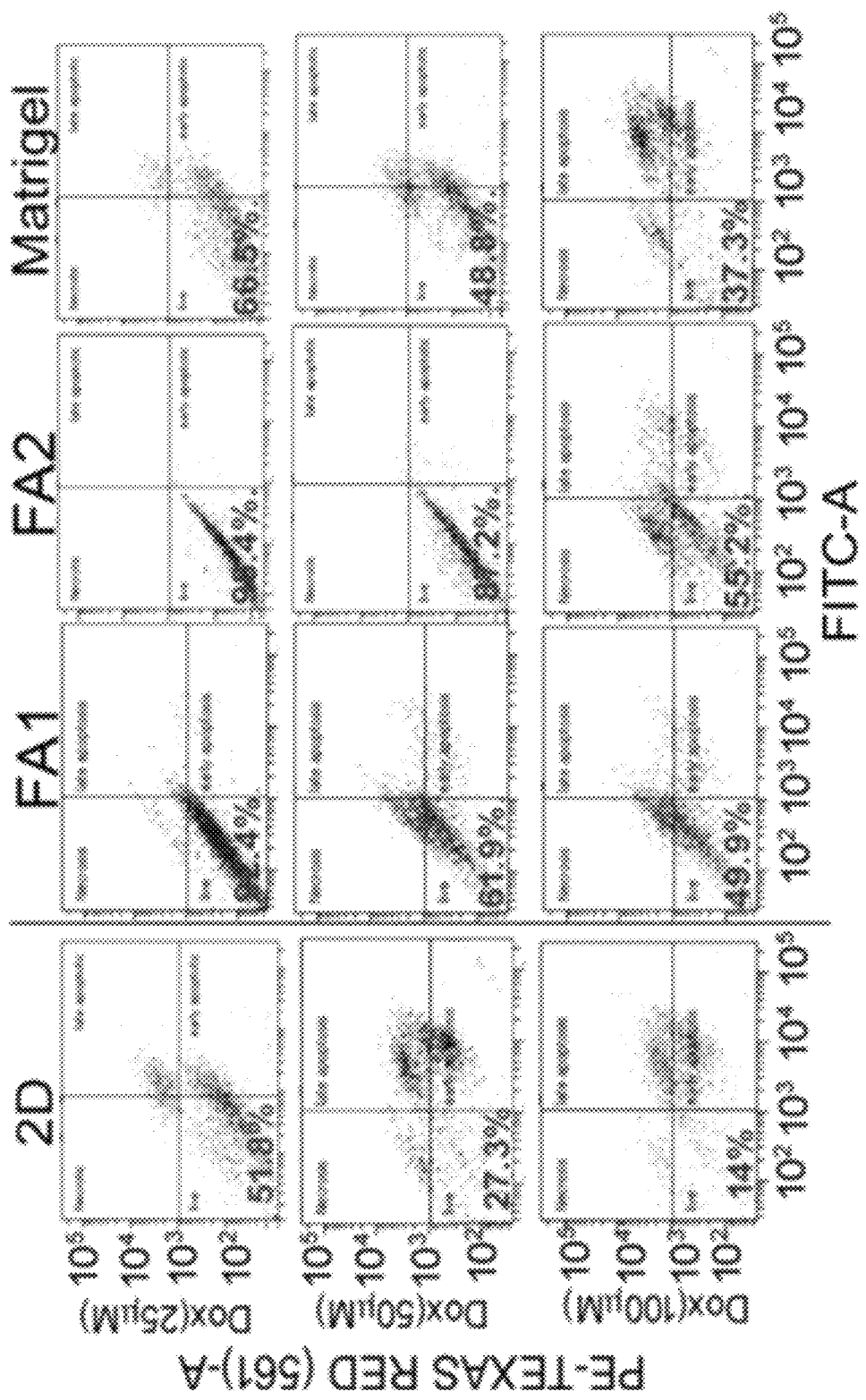

Example 22: Flow-Cytometry Analysis for Drug Testing on Breast Cancer Organoids/Tumoroids For relative quantification of cytotoxicity and apoptosis in the presence of these drugs, flow cytometry measurement was performed using Annexin V-FITC apoptosis detection kit (Sigma, USA). To do that, spheroids were cultured for 7 days (~$10^6$ cells). The cells were then treated each with 0-100 µM doxorubicin and only buffer for 24 hrs. After incubation, the spheroids were disintegrated, centrifuged and used for cell death assay using Annexin V-FITC Apoptosis detection kit (APOAF, Sigma, USA). Subsequently, the pellet was washed with PBS and further resuspended in 1× binding buffer. Cells were further stained with Annexin V-FITC and propidium iodide (PI) according to manufacturer's protocol. Unstained cells were used as a control (without Annexin V-FITC and PI) and cells stained with either Annexin V-FITC or PI was treated as fluorescent compensation controls. Quantification of Annexin V-FITC and PI staining were performed in a flow cytometer (FACS Aria, BD Biosciences, San Jose, CA) and analyzed using the BD FACS Diva software. For each sample, 20,000 cells were analyzed (FIG. 19D).

Example 23: Encapsulation of Biologic Substance into Functional Amyloid Hydrogel Entrapment/loading of drug/protein in functional amyloid hydrogel: The formed hydrogel was vortexed to obtain sol. 650 µM of rhodamine-tagged doxorubicin (DOX) and 2.5 mM of trans-retinoic acid (RA) was mixed with 20 µl of hydrogel sol. The sol-drug/protein mixture was kept for gel formation at RT.

Hydrogel formation was tested by tube inversion test as described previously. Upon gel formation the drug/protein was entrapped within the gel.

Evaluation of drug/protein loading in hydrogel: FTIR study was performed with amyloid hydrogels encapsulated with DOX and RA. The functional amyloid hydrogels without drug/protein was used as control. FIG. 20A shows the entrapment of drug/protein in the functional amyloid hydrogel. The results showed that the majority of secondary structure of hydrogel and the β-sheet structure remained similar to that of the control hydrogels in presence of drug/protein (FIG. 20A).

TEM was also performed with DOX and RA loaded hydrogel to verify fibril formation by functional amyloid hydrogels in the presence of drug and small molecule (FIG. 20B).

Example 24: In Vitro Release Profile of the Encapsulated Biologic Substance

To initiate drug release, 1 mL of phosphate buffer solution, pH 7.4 was layered on the hydrogel surface with only one surface exposed for the drug release. At regular time intervals, 100 µl of PBS was removed and the amount of drugs/protein released from the hydrogel was measured using fluorescence. The quantified in vitro drug release from the amyloid hydrogels is depicted in FIG. 21.

Example 25: Determining the Efficacy of the Designed Hydrogels as Drug/Protein Delivery Vehicles in Cells MDA-MB-231, breast cancer cell line was used for determining the efficacy of DOX release. To do so, MDA-MB-231 cells were grown on the DOX encapsulated hydrogels at a density of 2×10000 and cultured in complete DMEM media for 24 hrs. After 24 hrs, the cell morphology was imaged and the viability was then quantified using 3-(4,5-dimethylthiazol-2-yl)-2,5-diphenyl tetrazolium bromide (MTT) assay. FIG. 22A phase contrast images of MDA-MB-231 cells treated with DOX encapsulated hydrogels. FIG. 22B shows showing cancer cell death in MDA-MB-231 cells in the presence of DOX encapsulated amyloid hydrogels as quantified by the MTT assay. For FACS analysis, MDAMB-231 cells were seeded on the hydrogel in the density 50,000 cells/well and allowed to grow for 24 hrs. Following the incubation, the cells were trypsinized and harvested in an eppendorf. The cell pellet was obtained by centrifugation and was resuspended in binding buffer. The percentage of apoptotic cells were measured by Annexin-PI staining method. 2 µl each of Annexin and PI was added to the resuspended cells and incubated for 5 mins before acquiring the results using FACS. FIG. 22C shows that only hydrogels exhibit viability greater than 95%, while on encapsulating DOX in the hydrogels resulted in decrease in cell viability. To determine the efficacy of RA released from the hydrogel, SH-SY5Y neuroblastoma cells were seeded on hydrogel encapsulated with and without RA at a density of $1×10^4$ and cultured in complete DMEM media. The cultures were maintained in a 37° C. incubator with a humidified atmosphere of 5% CO2 for 48 hrs. After 48 hrs, the morphology of these cells was analyzed by phase contrast images (FIG. 23A) and the cell shape was quantified by circularity using Image J software (FIG. 23C).

The SH-SY5Y cells grown on hydrogel were immunostained with β-III tubulin (β-IIIT), a neuron specific marker to determine the efficacy of the released RA (FIG. 23B). The gene expression studies were done to verify the differentiation ability of SH-SY5Y on induction by RA. To investigate the expression profile of TUBB3 and ENO gene, which are the neuronal markers. The RNA isolation was done by Trizol Method and cDNA was synthesized in accordance to the manufacturer's protocol from 2D culture of SH-SY5Y. The gene expression was analyzed by Real-time PCR technique. TUBB3 and ENO gene were found to be up-regulated in all the cases (FIG. 23D).

Example 26. To Study the Efficacy of Designed Hydrogels as Insulin Delivery Vehicles in Diabetic Rats The functional amyloid hydrogel encapsulated with insulin (5 mg/ml) was administered subcutaneously to the diabetic rat model. Blood samples were collected from the tail veins of rats prior to drug administration and at different time intervals after dosing. Diabetes model rats were fasted for 12 h prior to and remained fasted during the experiment, but were allowed water ad libitum. The blood glucose level was checked biochemically at regular interval. The insulin released from the hydrogel in vivo was also monitored. To do that, blood samples were centrifuged (10,000 rpm, 4° C. for 15 min) and subsequently quantified using an appropriate insulin ELISA kit and during various time intervals. The only hydrogel (FA1) and buffer control (PBS) did not result in lowering of the blood glucose level. However, Formulation 1 (FA1 hydrogel+ insulin (10 mg/ml)), Formulation 2 (FA1 hydrogel+ insulin (5 mg/ml)), Formulation 3 (FA2 hydrogel+ insulin (10 mg/ml)) and Formulation 4 (FA2 hydrogel+ insulin (5 mg/ml)) showed sustained release of insulin from the depot and maintained the blood glucose level and serum insulin level over a period of time. Whereas, in the case of only insulin control, the blood glucose level and the serum insulin level was not maintained beyond 6 hrs after administration (FIGS. 24A and 24B).

Example 27. Wound Healing Activity of Functional Amyloid Hydrogels Using Fibroblast Cell Line Through In Vitro Scratch Assay To perform in vitro scratch assay, L929 cells (50,000 cells/well) were seeded onto 12-well cell culture plates in DMEM supplemented with 10% FBS/antibiotics and kept in a humidified CO2 incubator for 24 h for adherence. Once cell confluency reached, the wound was made by using a 200-μl sterile pipette tip. Further, it was washed with PBS and then wound was covered with hydrogel encapsulated with fibroblast growth factor (b-FGF2) and incubated for 5 mins for solidification. Wells were further incubated with a medium containing 1% FBS with or without the hydrogels. At different time points (0, 12, 24 and 48 h), the images of wound closure was captured using a phase-contrast microscope. The introduction of a scratch stimulated the cells at the edge of the scratch to proliferate and migrate towards the centre of the wound. It was observed that the area of scratch was completely filled by cell migration within 36 hrs in presence of FA1 and FA2 hydrogel. However, in case of control where no hydrogel was layered onto the scratch, the wound area did not show significant closure in 36 hrs (FIG. 25).

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the appended claims. The invention is, therefore, to be limited only by the terms of the appended claims along with the full scope of equivalents to which the claims are entitled.

The invention claimed is:

1. A functional amyloid hydrogel comprising functional amyloid nano-fibril peptides having a sequences selected from the group consisting of KLMEI, KLLDI, AVVLS, FVQWL, NLLFN and LVTLF, wherein the hydrogel is thixotropic.

2. The functional amyloid hydrogel of claim 1, wherein the nano-fibril peptides are non-toxic amyloid protein sequences.

3. The functional amyloid hydrogel of claim 1, wherein one end of said nano-fibril peptides is Fmoc capped.

4. A method of preparing the hydrogel of claim 1, the method comprising the steps of
   a. preparing a solution comprising a peptide having a sequences selected from the group consisting of KLMEI, KLLDI, AVVLS, FVQWL, NLLFN and LVTLF; and
   b. altering one or more chemical or physical characteristic of the solution, to provide the hydrogel, wherein the characteristic is selected from a group consisting of temperature, pH and ionic strength.

5. A method of preparing a scaffold for cell adhesion, the method comprising growing of cells on the functional amyloid hydrogel of claim 1.

6. A method for preparing spheroids and/or tumoroids for use as 3-dimensional tumor models, the method comprising:
   a. dissolving the functional amyloid hydrogels of claim 1 to provide a solution of the hydrogels;
   b. mixing the solution of the hydrogels with cells and incubating the cell-hydrogel mixture; and
   c. culturing the mixture containing a solidified hydrogel in a medium to provide the spheroids and/or tumoroid.

7. The method of claim 6, wherein said cells are cancerous or tumor cells selected from human breast cancer cells, lung cancer cells, cervical cancer cells, and liver cancer cells.

8. The method of claim 6, wherein said cells are a population of cells isolated from an animal tumor and are not incubated in cell culture medium before contact with the hydrogel.

9. A method for preparing a delivery agent for a biologic, the method comprising:
   a. dissolving the functional amyloid hydrogels of claim 1 to provide a solution of the hydrogels;
   b. mixing the biologic with the solution of the hydrogels to provide a mixture solution; and
   c. maintaining the mixture solution at room temperature for 10-30 minutes to provide the delivery agent for a biologic.

10. The method of claim 9, wherein the biologic is selected from small molecules, a peptide, a protein, a drug, and a therapeutic agent.

11. A method of wound healing, comprising contacting a wound with a composition comprising the functional amyloid hydrogel of claim 1, wherein the functional amyloid hydrogel comprises biological agents.

12. The method of claim 11, wherein the biological agents include growth factors.

13. The method of claim 11, comprising treating a wound introduced in confluent cells.

14. The functional amyloid hydrogel of claim 1 comprising functional amyloid non-fibril peptides having a sequence selected from the group consisting of KLMEI, AVVLS, FVQWL, NLLFN and LVTLF, wherein the hydrogel is thixotropic.

15. The functional amyloid hydrogel of claim 14, wherein the nano-fibril peptides are non-toxic amyloid protein sequences.

16. The functional amyloid hydrogel of claim 14, wherein one end of said nano-fibril peptides is Fmoc capped.

17. The functional amyloid hydrogel of claim 1 comprising functional amyloid non-fibril peptides having a sequence selected from the group consisting of KLMEI, AVVLS, and NLLFN, wherein the hydrogel is thixotropic.

18. The functional amyloid hydrogel of claim 17, wherein the nano-fibril peptides are non-toxic amyloid protein sequences.

19. The functional amyloid hydrogel of claim 17, wherein one end of said nano-fibril peptides is Fmoc capped.

\* \* \* \* \*